US010889860B2

(12) United States Patent
Ng et al.

(10) Patent No.: US 10,889,860 B2
(45) Date of Patent: Jan. 12, 2021

(54) COMPOSITIONS AND METHODS FOR SINGLE G-LEVEL HLA TYPING

(71) Applicant: Georgetown University, Washington, DC (US)

(72) Inventors: Jennifer Ng, Rockville, MD (US); Carolyn K. Hurley, Bethesda, MD (US); Bin Tu, Randallstown, MD (US); Carly Masaberg, Randallstown, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 502 days.

(21) Appl. No.: 15/023,552

(22) PCT Filed: Sep. 24, 2013

(86) PCT No.: PCT/US2013/061377
§ 371 (c)(1),
(2) Date: Mar. 21, 2016

(87) PCT Pub. No.: WO2015/047220
PCT Pub. Date: Apr. 2, 2015

(65) Prior Publication Data
US 2016/0208325 A1   Jul. 21, 2016

(51) Int. Cl.
*C12Q 1/68* (2018.01)
*C12Q 1/6881* (2018.01)

(52) U.S. Cl.
CPC ..... *C12Q 1/6881* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 5,910,413 A * | 6/1999 | Garey | .................. | C12Q 1/6858 435/6.11 |
| 6,194,147 B1 | 2/2001 | Baxter-Lowe et al. | | |
| 2002/0197613 A1 | 12/2002 | Canck et al. | | |
| 2003/0050470 A1 * | 3/2003 | An | ......................... | C07H 21/00 536/24.3 |
| 2004/0023207 A1 * | 2/2004 | Polansky | ............... | A61K 31/00 435/5 |
| 2007/0065860 A1 * | 3/2007 | Hildebrand | .......... | C12Q 1/6876 435/6.11 |
| 2009/0099035 A1 | 4/2009 | Petersdorf et al. | | |
| 2009/0208947 A1 * | 8/2009 | Wang | ................... | C12Q 1/6853 435/6.12 |
| 2010/0261189 A1 * | 10/2010 | Bentley | ................ | C12Q 1/6869 435/6.11 |
| 2011/0002948 A1 * | 1/2011 | Sayer | ................... | C12Q 1/6881 424/184.1 |

FOREIGN PATENT DOCUMENTS

| | | | | | |
|---|---|---|---|---|---|
| CN | 101892317 A | * | 11/2010 | | |
| CN | 101921840 A | * | 12/2010 | ........... | C12Q 1/6869 |
| CN | 101962676 A | * | 2/2011 | | |
| EP | 0892069 A2 | * | 1/1999 | ........... | C12Q 1/6881 |
| EP | 2186911 A1 | * | 5/2010 | ........... | C12Q 1/6881 |
| EP | 2272986 | * | 1/2011 | ............... | C12Q 1/68 |
| EP | 2314715 A2 | * | 4/2011 | ........... | C12Q 1/6881 |
| WO | WO-2012000152 A1 | * | 1/2012 | ........... | C12Q 1/6869 |

OTHER PUBLICATIONS

Hoppe et al. Sequencing based typing of HLA. Bone Marrow and Stem Cell Transplantation. Methods in Molecular Medicine, vol. 134 2007, pp. 71-79. Humana Press Inc. (Year: 2007).*
Dalva et al. HLA typing with sequence-specific oligonucleotide primed PCR (PCR-SSO) and use of Luminex Technology. Bone Marrow and Stem Cell Transplantation. Methods in Molecular Medicine, vol. 134 2007, pp. 61-69. Humana Press Inc. (Year: 2007).*
Testi M, Iannelli S, Testa G, Troiano M, Capelli S, Fruet F, Federici G, Bontadini A, Andreani M. Evaluation of DRB1 high resolution typing by a new SSO-based Luminex method. Mol Biol Rep. Jan. 2012; 39(1):13-6. Epub Mar. 22, 2011. (Year: 2011).*
Dunbar SA. Applications of Luminex xMAP technology for rapid, high-throughput multiplexed nucleic acid detection. Clin Chim Acta. Jan. 2006; 363(1-2):71-82. Epub Aug. 15, 2005. (Year: 2005).*
Adams SD, Barracchini KC, Chen D, Robbins F, Wang L, Larsen P, Luhm R, Stroncek DF. Ambiguous allele combinations in HLA Class I and Class II sequence-based typing: when precise nucleotide sequencing leads to imprecise allele identification. J Transl Med. Sep. 13, 2004; 2(1):30. (Year: 2004).*
Cao K, Chopek M, Fernández-Viña MA. High and intermediate resolution DNA typing systems for class I HLA-A, B, C genes by hybridization with sequence-specific oligonucleotide probes (SSOP). Rev Immunogenet. 1999; 1(2):177-208. (Year: 1999).*
English Translation of CN101892317 published Nov. 24, 2010. (Year: 2010).*
SantaLucia Jr, John. Physical principles and visual-OMP software for optimal PCR design. PCR Primer Design. Humana Press, 2007: pp. 3-33. (Year: 2007).*

(Continued)

*Primary Examiner* — Teresa E Strzelecka
*Assistant Examiner* — Olayinka A Oyeyemi
(74) *Attorney, Agent, or Firm* — Lathrop GPM LLP; Alan W. Steele

(57) ABSTRACT

Provided are methods, kits, and systems useful in the performance of analysis and reporting of highly polymorphic loci, including, in particular, the performance of analysis and reporting of HLA typing. Combining one-step sequencing and sequence-specific oligonucleotide probe hybridization, the methods, kits, and systems offer improved efficiency of HLA typing while providing detailed sequencing information. In certain embodiments the methods and systems comprise one or more software applications to facilitate data acquisition, processing, and reporting.

24 Claims, 2 Drawing Sheets
Specification includes a Sequence Listing.

(56) References Cited

OTHER PUBLICATIONS

Shiina et al. Super high resolution for single molecule-sequence-based typing of classical HLA loci at the 8-digit level using next generation sequencers. Tissue Antigens. Oct. 2012; 80(4):305-16. Epub Aug. 4, 2012. (Year: 2012).*

Genbank Accession No. NT_007592—*Homo sapiens* chromosome 6 genomic scaffold, GRCh38.p13 Primary Assembly HSCHR6_CTG1, retrieved on Feb. 3, 2020 from http://www.ncbi.nlm.nih.gov/nuccore/NT_007592). (Year: 2012).*

Ota, M. et al., "Validation of sensitive human leukocyte antigen-sequence-specific primer and probe typing in forensic DNA examination", *Legal Medicine*, 8(4):203-209 (Elsevier Ireland Ltd., 2006).

International Search Report and Written Opinion from parent PCT application PCT/US2013/061377 dated Jan. 7, 2014.

* cited by examiner

SEQUENCE LISTING

<160> NUMBER OF SEQ ID NOS: 54

<210> SEQ ID NO 1
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 1
gcagggcgga acctcagagt cactctct                28

```
<210> SEQ ID NO 2
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 2
ccatccccgg cgacctatag gagatg                                        26

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
aggccatccc gggcgatcta t                                             21

<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 4
ggagatgggg aaggctcccc act                                           23

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
cccagacgcc gaggatggcc g                                             21

<210> SEQ ID NO 6
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 6
gcacccaccc ggactcagaa tctcct                                        26

<210> SEQ ID NO 7
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 7
gggtcccagt tctaaagtcc ccacg                                         25

<210> SEQ ID NO 8
<211> LENGTH: 21
<212> TYPE: DNA
<213> ORGANISM: Artificial sequence
<220> FEATURE:
```

<223> OTHER INFORMATION: Synthetic oligonucleotide

<400> SEQUENCE: 8
agcgaggkgc ccgcccggcg a                                              21

<210> SEQ ID NO 9
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 9
ccgaaccstc ctcctgctgc tct                                            23

<210> SEQ ID NO 10
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 10
caggaaacag ctatgacccc aacccaaagt cccc                                34

<210> SEQ ID NO 11
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 11
tgtaaaacga cggccagccc gcagagaatt ac                                  32

<210> SEQ ID NO 12
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 12
caggaaacag ctatgacgca gggtcatggg cc                                  32

<210> SEQ ID NO 13
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 13
caggaaacag ctatgacgca gggtcacggc ct                                  32

<210> SEQ ID NO 14
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 14
tgtaaaacga cggccagttc ctcgcagagg atttcg                              36

<210> SEQ ID NO 15
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 15
caggaaacag ctatgaccgt gcggagctcc aactg     35

<210> SEQ ID NO 16
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 16
caggaaacag ctatgacctc tcctctgcar gatccc     36

<210> SEQ ID NO 17
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 17
ggtgggtgct gttgaaggt     19

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
acacacacac tcagattccc a     21

<210> SEQ ID NO 19
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 19
tggtgggcgt tggggcg     17

<210> SEQ ID NO 20
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 20
caggaaacag ctatgaccca ctcacctcgc ckctgcac     38

<210> SEQ ID NO 21
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 21
actcacctcg cckctgcac					19

<210> SEQ ID NO 22
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 22
tgtaatacga cggccagttt cttggaggag gttaagtt					38

<210> SEQ ID NO 23
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 23
tgtaaaacga cggccagttt cttgtggcag cttaagtt					38

<210> SEQ ID NO 24
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 24
tgtaatacga cggccagttt cctgtggcag cctaagagg					39

<210> SEQ ID NO 25
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 25
tgtaaaacga cggccagtat cttggagtac tctacgtc					38

<210> SEQ ID NO 26
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 26
tgtaatacga cggccagttt cttggagcag gttaaaca					38

<210> SEQ ID NO 27
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 27
tgtaaaacga cggccagtgg cagggtaagt ata					33

<210> SEQ ID NO 28
<211> LENGTH: 37

```
<212> TYPE: DNA
<213> ORGANISM: Artificial sequence
<220> FEATURE:
<223> OTHER INFORMATION: Synthetic oligonucleotide

<400> SEQUENCE: 28
tgtaaaacga cggccagttc ttggagtact ctacggg                    37

<210> SEQ ID NO 29
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 29
tgtaatacga cggccagttt cttgaagcag ga                         32

<210> SEQ ID NO 30
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 30
tgttggtccc aattgtctcc cctc                                  24

<210> SEQ ID NO 31
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 31
ggaggccatc cccggcgacc tat                                   23

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
tcggacccgg agactgtg                                         18

<210> SEQ ID NO 33
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 33
gaaacsgcct ctgyggggag aagcaa                                26

<210> SEQ ID NO 34
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 34
```
gggaggagcg aggggaccsc ag                                                    22

<210> SEQ ID NO 35
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 35
gtttcatttt cagtttaggc ca                                                    22

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
gcctctgygg ggagaagcaa                                                       20

<210> SEQ ID NO 37
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 37
ggttggtygg ggc                                                              13

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 38
ggkccagggt ctcaca                                                           16

<210> SEQ ID NO 39
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 39
aggctcccca ctg                                                              13

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
gggtcgggcg ggtctcagcc                                                       20

<210> SEQ ID NO 41
<211> LENGTH: 15
<212> TYPE: DNA
<213> ORGANISM: Artificial sequence

```
<220> FEATURE:
<223> OTHER INFORMATION: Synthetic oligonucleotide

<400> SEQUENCE: 41
ggagccgcgc aggga                                                  15

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ggaggggtcg tgacctgcgc                                             20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tgaccrcggg ggccggggcc                                             20

<210> SEQ ID NO 44
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 44 gtggggatg rggaggggt                                               19

<210> SEQ ID NO 45
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 45
cacgtggcag gtgtagacg                                              19

<210> SEQ ID NO 46
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 46
gtgacagatt tctatccag                                              19

<210> SEQ ID NO 47
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 47
gtgtcttctc aggaggc                                                17
```

```
<210> SEQ ID NO 48
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 48
cgccccgcgc cgcgctcac                                                    19

<210> SEQ ID NO 49
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 49
ggatctcgga cccggag                                                      17

<210> SEQ ID NO 50
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 50
tgtaaaacga cggccag                                                      17

<210> SEQ ID NO 51
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 51
caggaaacag ctatgac                                                      17

<210> SEQ ID NO 52
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 52
tccccactgc ccytggtac                                                    19

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
tcagtgtctt ctcaggaggc                                                   20

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 54
cagctcacag ggactcag                                                    18
```

COMPOSITIONS AND METHODS FOR SINGLE G-LEVEL HLA TYPING

GOVERNMENT SUPPORT

This invention was made with government support under grant numbers N0014-08-1-1078, N00014-10-1-0199, N00014-11-1-0590, N00014-12-1-0240, and N00014-13-1-0210 awarded by the Office of Naval Research. The government has certain rights in the invention.

RELATED APPLICATIONS

This application is the U.S. national phase of International Patent Application No. PCT/US2013/061377, filed Sep. 24, 2013.

SEQUENCE LISTING

This application incorporates by reference the entire contents of the 11 kilobyte ASCII text file named GUX-037.25 ST.25.txt, created on Sep. 24, 2013, which contains a sequence listing.

BACKGROUND OF THE INVENTION

Human major histocompatibility (MHC) genes, also termed human leukocyte antigen (HLA) genes, are among the most polymorphic genes known in the human genome. HLA proteins are encoded by a series of closely linked genes located at the position p21 on chromosome 6. Genes of the HLA region span approximately 4 million base pairs of DNA and are clustered into three distinct regions designated class I, class II, and class III. Genes within the class I and class II regions share structural and functional properties and are considered to be part of the immunoglobulin gene superfamily. Although distinct in sequence and structure, both class I and class II genes encode proteins that are critical in controlling T-lymphocyte and natural killer cell recognition and determining histocompatibility in marrow and other tissue or organ transplantation. Rammensee H G, Curr. Opin. Immunol. 7:85-96 (1995).

At least 17 loci, including several pseudogenes, exist in the HLA class I region. Three of these loci encode HLA-A, -B, and -C alloantigens that constitute the major class I determinants important for matching in tissue transplantation. The HLA-A, -B, and -C loci show a striking degree of sequence and structural homology with one and another, and genes at all three loci are highly polymorphic. Bodmer J G et al., Tissue Antigens 49:297-321 (1997). More than 2300 HLA-A, 3000 HLA-B, and 1800 HLA-C alleles have been described. In addition, other class I genes have been defined. Although structurally homologous with HLA-A, B and C genes, these additional class I genes appear to have limited polymorphism, the tissue expression of their encoded molecules is more restricted, their potential role as transplantation antigens is unknown, or they do not specify functional proteins.

The HLA class II region includes nine distinct genes: DRA, DRB1, DRB3, DRB4, DRB5, DQA1, DQB1, DPA1, and DPB1. Six additional class II genes or gene fragments have been described but these are either nonfunctional pseudogenes or do not encode proteins known to participate in transplant-related immune interactions. As with class I genes, class II DR, DQ, and DP genes show a striking degree of polymorphism, with more than 1300 alleles thus far defined at the DRB1 locus.

The identification of HLA alleles has significance in both medical clinics and genetic research. They play a role in tissue and organ transplantation, susceptibility to autoimmune diseases, and hypersensitivity reactions to certain drugs. In addition, detection of HLA polymorphisms and their frequencies in populations is the key to study fundamental issues in immunogenetics, such as evolutionary diversification of the HLA system and the linkage between certain HLA types and disease susceptibility.

The clinical importance of the identification of HLA polymorphisms can be illustrated by its application in hematopoietic progenitor cell (e.g., bone marrow) transplantation. Selection of HLA allele identity (i.e., matching) between patients and potential tissue donors has proven essential for the success of unrelated marrow transplantation for hematologic malignancies and other fatal blood diseases. Spellman S et al., Blood 120:259-265 (2012). Current standards for HLA typing predominately employ DNA-based methods for identifying HLA-A, -B, and -C alleles, and DNA-based typing for class II HLA-DRB1. Typing of other HLA loci such as DQB1 and DPB1 alleles is considered important in certain circumstances such as when a partially matched donor will be chosen or if the recipient is sensitized to HLA differences. DNA-based methods include DNA sequencing, amplification and hybridization methods, and these remain the most accurate when compared to the older serological method.

Optimization of the outcome of unrelated hematopoietic progenitor cell transplantation requires comprehensive analysis of both HLA class I and class II genes of transplant populations and potential donors or umbilical cord blood units. To that end, a national donor registry is maintained by the National Marrow Donor Program (NMDP). The NMDP currently lists the HLA assignments from more than 10 million individuals and nearly 185,000 cord blood units. Volunteers joining an unrelated donor registry such as the NMDP's Be The Match Registry are usually typed for HLA-A, -B, and -DRB1 at recruitment. These assignments are usually at intermediate resolution to limit typing costs so that many volunteers can be added to the registry. As a consequence, searches identify potentially matched donors who must then undergo further HLA typing at a higher resolution and for additional loci (HLA-C, -DQB1, and -DPB1) to identify an optimal donor for a specific patient. The inability of the physician to directly identify an HLA allele-matched donor from the registry is one barrier to timely transplantation and impacts its outcome. Some patients may progress to stages of their disease while waiting to receive identification of a matched donor/cord blood unit where transplantation is no longer an option, or to a stage where the outcome of transplantation is negatively impacted.

Nomenclature for specific HLA alleles has evolved, and continues to evolve, to incorporate ever-increasing complexity as typing methods and typing resolution improve and as new alleles are discovered. Although DNA-based typing offers the possibility of unambiguous assignment, from a practical application standpoint, most typing methods provide ambiguous results. The complexity of the nomenclature, coupled with the ambiguity, make this information difficult to utilize in registry donor search algorithms and difficult to communicate to the end users of the data (i.e., physician or transplant coordinator).

SUMMARY OF THE INVENTION

The invention concerns methods, kits, and systems useful in the performance of analysis and reporting of highly polymorphic loci, including, in particular, the performance of analysis and reporting of HLA typing. Information obtained using the invention is useful for any of several applications, including, without limitation, typing of volunteers for entry onto unrelated donor or umbilical cord blood registries; typing of potential recipients and potential donors for cell, tissue, and organ transplantation (e.g., hematopoietic progenitor cell transplant, adoptive cell therapies, and solid organ transplantation); and typing of individuals to assess risk for specific diseases (e.g., autoimmune diseases) or treatment outcomes (e.g., hypersensitivity to specific drugs). The invention is useful for small to high volume applications. In one embodiment, the invention can be performed in high throughput manner.

In certain aspects the invention provides for increased resolution of genotypes. The work flow and assays used provide HLA assignments at a resolution that includes single HLA G-group genotypes. This resolution is identical to or very similar to the level of resolution needed to select an "allele-match" in transplantation or to identify a risk associated genotype. Currently identification of a single HLA genotype for an individual requires the separation of alleles by either sequence-specific polymerase chain reaction primers or DNA cloning. The former requires a panel of primers that preferentially anneal to intron sequences and are capable of amplifying a single allele in each potential diploid allele combination. Its limitation is that multiple PCR reactions must be simultaneously performed for each sample and a second PCR reaction may be required if the initial primer panel is insufficient to obtain single alleles. Cloning is not a standard technique in clinical laboratories and is a time-consuming procedure that requires several clones to be sequenced to eliminate sequence artifacts. Next generation DNA sequencing strategies might also be used to separate alleles, but the platforms, strategies, and software are still under development and most laboratories do not have the technology in house.

In certain aspects the invention provides confirmation of results, enhanced accuracy, and reduced effort for DNA sequencing results. The combination of information from DNA sequencing and oligonucleotide probe hybridization provides a confirmation of DNA sequencing results without the need for intensive data review by laboratory staff, thus saving time and money while providing highly accurate data.

Additional features and advantages of the invention include improved probe hybridization specificity and accuracy of HLA assignments by combining its use with DNA sequencing; improved merger of DNA sequencing and oligonucleotide probe hybridization data; and ability to provide primary DNA sequence data to provide a long-term solution to loss of information and outdated HLA assignments.

An aspect of the invention is a kit comprising a first set of oligonucleotide primers for polymerase chain reaction (PCR) amplification of at least one human leukocyte antigen (HLA) class I locus, at least one HLA class II locus, or both at least one HLA class I locus and at least one HLA class II locus of a subject; and a second set of oligonucleotide primers for performing one-step DNA sequencing of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject.

In one embodiment, the first set of oligonucleotide primers comprises oligonucleotide primers having nucleotide sequences selected from the group consisting of SEQ ID NOs 1-29.

In one embodiment, the second set of oligonucleotide primers comprises oligonucleotide primers having nucleotide sequences selected from the group consisting of SEQ ID NOs 4 and 30-54.

In one embodiment, the first set of oligonucleotide primers comprises oligonucleotide primers having nucleotide sequences selected from the group consisting of SEQ ID NOs 1-29, and the second set of oligonucleotide primers comprises oligonucleotide primers having nucleotide sequences selected from the group consisting of SEQ ID NOs 4 and 30-54.

An aspect of the invention is a system comprising a first set of oligonucleotide primers for polymerase chain reaction (PCR) amplification of at least one human leukocyte antigen (HLA) class I locus, at least one HLA class II locus, or both at least one HLA class I locus and at least one HLA class II locus of a subject; a second set of oligonucleotide primers for performing one-step DNA sequencing of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject; and a set of oligonucleotide probes for performing sequence-specific probe hybridization of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject.

In one embodiment, the system further comprises a computer program product residing on a non-transitory computer-readable medium having a plurality of instructions stored thereon which, when executed by a computer processor, cause that computer processor to:

(a) assemble, from one or more input nucleotide sequences for any one HLA class I locus or HLA class II locus, a single contiguous nucleotide sequence for each allele of said locus, thereby generating one or two single contiguous nucleotide sequences for said locus;

(b) compare the one or two assembled single contiguous nucleotide sequences to a database associating nucleotide sequences with corresponding HLA alleles; and (c) output a list of HLA genotypes compatible with the one or two assembled single contiguous nucleotide sequences for said locus. For example, if sequence-based typing (SBT) gives 1+2 or 3+4 and hybridization gives 1+2 or 5+6 or 7+8, the program gives the overlapping genotype 1+2 as the final assignment. The 1+2 is the G-level assignment. This produces a result that has a higher resolution than the assignment achieved by either pathway (i.e., SBT or hybridization) alone.

In one embodiment, the system further comprises a computer program product residing on a non-transitory computer-readable medium having a plurality of instructions stored thereon which, when executed by a computer processor, cause that computer processor to:

(a) compare (i) input HLA assignments based on nucleotide sequence information for the at least one HLA class I locus, the at least one HLA class II locus, or both the at least one HLA class I locus and the at least one HLA class II locus and (ii) input HLA assignments based on hybridization data for the at least one HLA class I locus, the at least one HLA class II locus, or both the at least one HLA class I locus and the at least one HLA class II locus;

(b) identify any discrepancies between the input HLA assignments based on nucleotide sequence information and the input HLA assignments based on hybridization data; and (c) identify those genotypes that are present in both the input HLA assignments based on nucleotide sequence information and the input HLA assignments based on hybridization data, and exclude those genotypes that are present in only one of the input HLA assignments based on nucleotide sequence information and the input HLA assignments based on hybridization data.

An aspect of the invention is a method for human leukocyte antigen (HLA) typing, comprising the steps of performing one-step DNA sequencing of at least one HLA class I locus or at least one HLA class II locus of a subject, thereby providing at least intermediate resolution typing for the at least one HLA class I locus or the at least one HLA class II locus; performing sequence-specific probe hybridization for the at least one HLA class I locus or the at least one HLA class II locus, thereby providing a second at least intermediate resolution typing for the at least one HLA class I locus or the at least one HLA class II locus; and assigning, based on results of the one-step DNA sequencing and the sequence-specific probe hybridization, a single G-level genotype for the at least one HLA class I locus or the at least one HLA class II locus of the subject.

An aspect of the invention is a method for human leukocyte antigen (HLA) typing, comprising the steps of amplifying DNA encoding at least one HLA class I locus or at least one HLA class II locus of a subject, thereby providing an amplicon of the at least one HLA class I locus or the at least one HLA class II locus of the subject; performing one-step DNA sequencing of the amplicon of the at least one HLA class I locus or the at least one HLA class II locus of the subject, thereby providing a first at least intermediate resolution typing for the at least one HLA class I locus or the at least one HLA class II locus; performing sequence-specific probe hybridization of the amplicon of the at least one HLA class I locus or the at least one HLA class II locus of the subject, thereby providing a second at least intermediate resolution typing for the at least one HLA class I locus or the at least one HLA class II locus; and assigning, based on results of the one-step DNA sequencing and the sequence-specific probe hybridization, a single G-level genotype for the at least one HLA class I locus or the at least one HLA class II locus of the subject.

An aspect of the invention is a method for human leukocyte antigen (HLA) typing, comprising the steps of performing one-step DNA sequencing of at least one HLA class I locus and at least one HLA class II locus of a subject, thereby providing a first at least intermediate resolution typing for the at least one HLA class I locus and the at least one HLA class II locus; performing sequence-specific probe hybridization for the at least one HLA class I locus and the at least one HLA class II locus, thereby providing a second at least intermediate resolution typing for the at least one HLA class I locus and the at least one HLA class II locus; and assigning, based on results of the one-step DNA sequencing and the sequence-specific probe hybridization, a single G-level genotype for the at least one HLA class I locus and the at least one HLA class II locus of the subject.

An aspect of the invention is a method for human leukocyte antigen (HLA) typing, comprising the steps of amplifying DNA encoding at least one HLA class I locus and at least one HLA class II locus of a subject, thereby providing an amplicon of the at least one HLA class I locus and an amplicon of the at least one HLA class II locus of the subject; performing one-step DNA sequencing of the amplicon of the at least one HLA class I locus and the amplicon of the at least one HLA class II locus of the subject, thereby providing a first at least intermediate resolution typing for the at least one HLA class I locus and the at least one HLA class II locus; performing sequence-specific probe hybridization of the amplicon of the at least one HLA class I locus and the amplicon of the at least one HLA class II locus of the subject, thereby providing a second at least intermediate resolution typing for the at least one HLA class I locus and the at least one HLA class II locus; and assigning, based on results of the one-step DNA sequencing and the sequence-specific probe hybridization, a single G-level genotype for the at least one HLA class I locus and the at least one HLA class II locus of the subject.

In one embodiment, the amplifying DNA encoding at least one HLA class I locus comprises a first amplification for use in performing the one-step DNA sequencing and a second amplification for use in performing the sequence-specific probe hybridization.

In one embodiment, the amplifying DNA encoding at least one HLA class II locus comprises a first amplification for use in performing the one-step DNA sequencing and a second amplification for use in performing the sequence-specific probe hybridization.

In one embodiment, the at least one HLA class I locus is selected from the group consisting of HLA-A, HLA-B, and HLA-C.

In one embodiment, the at least one HLA class I locus comprises HLA-A and HLA-B.

In one embodiment, the at least one HLA class I locus comprises HLA-A, HLA-B, and HLA-C.

In one embodiment, the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class II locus comprises HLA-DRB1.

In one embodiment, the at least one HLA class I locus comprises HLA-A and HLA-B, and the at least one HLA class II locus comprises HLA-DRB1.

DETAILED DESCRIPTION

Figure 1:
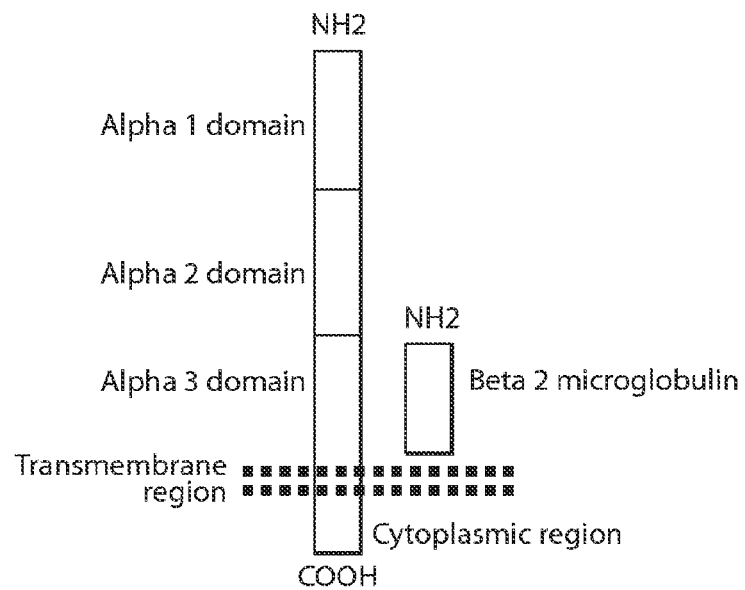
FIG. 1 is a schematic drawing depicting the structure of a class I molecule. NH2, amino terminal end; COOH, carboxy terminal end.

The invention overcomes a number of problems in HLA typing by taking advantage, for the first time, of the power of combined methods of DNA sequencing and probe hybridization. The efficiency made possible by the combined methods of DNA sequencing and probe hybridization can be further enhanced by the application of high throughput methods, including robotic automation, and computer software described herein.

Workflow Overview

Methods and compositions of the invention relate to various aspects of the following workflow summary. Not every step or feature of the workflow summary is necessarily included in the various methods and compositions of the invention. Different features of the workflow summary are described in greater detail below.

A biological sample is obtained from an individual. Genomic DNA is prepared from the biological sample. Genomic DNA is divided to enter parallel or, in some embodiments, serial DNA sequencing and probe hybridization pathways.

In the DNA sequencing pathway, desired exons of specific HLA genes are amplified in a polymerase chain reaction (PCR) using sequence-specific (locus-specific) oligonucleotide primers. No attempt is made to separate alleles for the PCR. Unincorporated primers and nucleotides are removed from amplification products. DNA amplicons may be assessed by gel electrophoresis. Sequencing reactions are set up using oligonucleotide primers to obtain DNA sequences of both sense and antisense strands of the exons to be sequenced. No attempt is made to separate alleles for the sequencing reactions. Sequence reactions are performed. Unincorporated primers and nucleotides are removed from sequence reaction products. Sequence reaction products are sequenced. Sequence data is collected and interpreted by software of the invention (Assign ATF software).

In the probe hybridization pathway, desired exons of specific HLA genes are amplified in a polymerase chain reaction (PCR) using sequence-specific (e.g., locus-specific) oligonucleotide primers. No attempt is made to separate alleles for the PCR. Unincorporated primers and nucleotides may be removed from amplification products. Sequence-specific oligonucleotide probe hybridization reactions using a panel of oligonucleotide probes with DNA sequences specific for the HLA genes being tested are set up and performed. Hybridization is measured. Hybridization data are collected and interpreted by software (e.g., Fusion™ software).

In an alternative embodiment, genomic DNA is amplified in a polymerase chain reaction (PCR) using sequence-specific (e.g., locus-specific) oligonucleotide primers before the sample is divided for the parallel DNA sequencing and probe hybridization pathways. In this embodiment, subsequent parallel PCRs are not required.

Data from the sequencing pathway can be used to assemble contiguous DNA sequences from shorter individual DNA sequences. In addition, data from the sequencing pathway can be used to assign DNA sequences to HLA genotypes compatible with the DNA sequences, thereby yielding at least intermediate resolution typing. In a preferred embodiment, one or both of the DNA sequence assembly and assigning is performed using purpose-built software in accordance with the invention. This sequence assembly and assigning software is referred to herein as Assign ATF software.

Data from the probe hybridization pathway is typically collected and processed by commercially available purpose-built software, e.g., Thermo Fisher Scientific Luminex® Fusion™ software. Using this software, data from the probe hybridization pathway can be used to eliminate HLA genotypes which are incompatible with the hybridization results, to assign HLA genotypes which are compatible with the hybridization results, or both to eliminate HLA genotypes which are incompatible with the hybridization results and to assign HLA genotypes which are compatible with the hybridization results.

In a preferred embodiment, data from the DNA sequencing pathway and data from the probe hybridization pathway are merged and analyzed using purpose-built software in accordance with the invention. In particular, the data merger and analysis software compares HLA assignments from the DNA sequencing pathway and the probe hybridization pathway and identifies any discrepancies. The software also compares HLA assignments from the DNA sequencing pathway and the probe hybridization pathway and (i) identifies those genotypes that are found as results in both pathways and (ii) excludes results that are found as results in only one of the two pathways. In one embodiment, this same data merger and analysis software of the invention is capable of tracking and associating individual sample identities with any or all categories of data and data interpretation in accordance with the invention. This data tracking, merger, and analysis software is referred to herein as Allelos software.

HLA molecules are proteins expressed on the surfaces of human cells and play an important role in transplantation. Because of this, HLA molecules of potential graft donors and potential recipient (i.e., patient) must be identified to find a suitable match.

Class I molecules are found on the surface of essentially all nucleated cells in the body. As shown in FIG. 1, class I protein molecules are heterodimers comprising a ca. 44 kDa polymorphic alpha chain and a ca. 12 kDa non-polymorphic beta-2 microglobulin chain. Approximately 0.5-1 million HLA class I molecules, including HLA-A, HLA-B, and HLA-C molecules, are expressed on the surface of any given nucleated cell.

Each class I alpha chain includes three extracellular domains (each approximately 100 amino acids in length), a transmembrane domain, and a cytoplasmic tail. The alpha 1 domain and the alpha 2 domain are principally involved in antigen presentation, and the vast majority of class I polymorphism resides in these two domains. Each alpha chain is initially synthesized with a leader peptide on its amino terminus; this leader peptide is removed from the alpha chain during transport to the cell surface.

Figure 2:
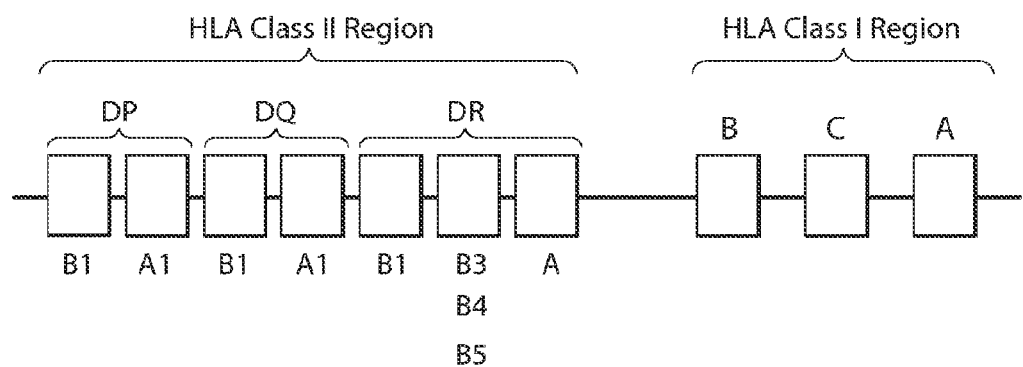
FIG. 2 is a schematic drawing depicting the structure of the human major histocompatibility gene complex (MHC) located on chromosome 6. A, B, and C in the HLA Class I Region represent loci encoding the alpha chain of HLA-A, -B, and -C, respectively. Also shown are the loci encoding the alpha (A) and beta (B) chains of HLA-DR, -DQ, and -DP.

The genes or loci that encode the HLA-A, -B, and -C alpha chains are located adjacent to one another in the major histocompatibility complex (MHC) on chromosome 6. See FIG. 2. The entire MHC encompasses approximately 3.5 million bases of DNA. The class I alpha 1 and alpha 2 domains are encoded by polymorphic exons 2 and 3, respectively. The gene encoding beta-2 microglobulin is on chromosome 15.

Figure 3:
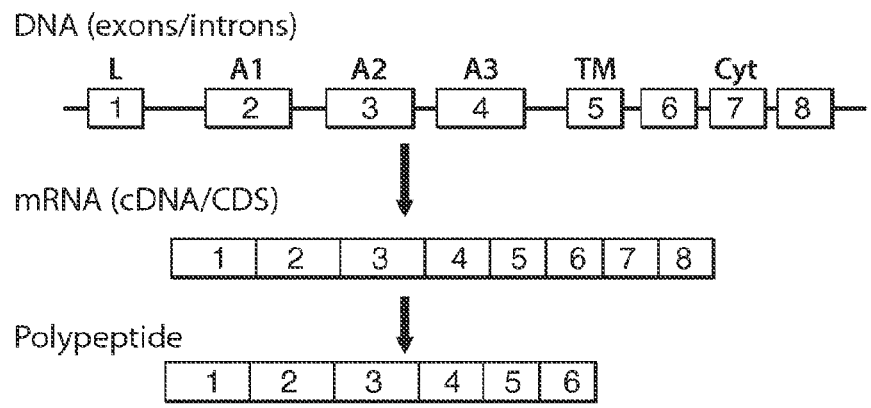
FIG. 3 is a schematic drawing depicting the structure of a class I alpha chain locus, corresponding mRNA, and corresponding polypeptide. In the DNA and mRNA, exons are depicted as numbered boxes, and introns flank the exons. In the polypeptide, numbered boxes correspond to structural and functional regions. L, leader; TM, transmembrane domain; Cyt, cytoplasmic domain.

Each alpha chain locus includes both exons and introns. During transcription and translation, sequences corresponding to introns are removed, and exons are apposed to arrive at a coding sequence for the polypeptide product. See FIG. 3. For example, the full length genomic DNA sequence for a particular HLA-A gene, HLA-A*01:01:01:01, is about 3200 nucleotides long, whereas the corresponding coding DNA sequence is about 1100 nucleotides long.

Each cell has both maternally and paternally inherited HLA-A alleles, both maternally and paternally inherited HLA-B alleles, and both maternally and paternally inherited HLA-C alleles. Because the genes encoding class I HLA molecules are co-dominant, each cell expresses HLA-A molecules encoded by both maternally and paternally inherited HLA-A alleles, HLA-B molecules encoded by both maternally and paternally inherited HLA-B alleles, and HLA-C molecules encoded by both maternally and paternally inherited HLA-C alleles.

Figure 4:
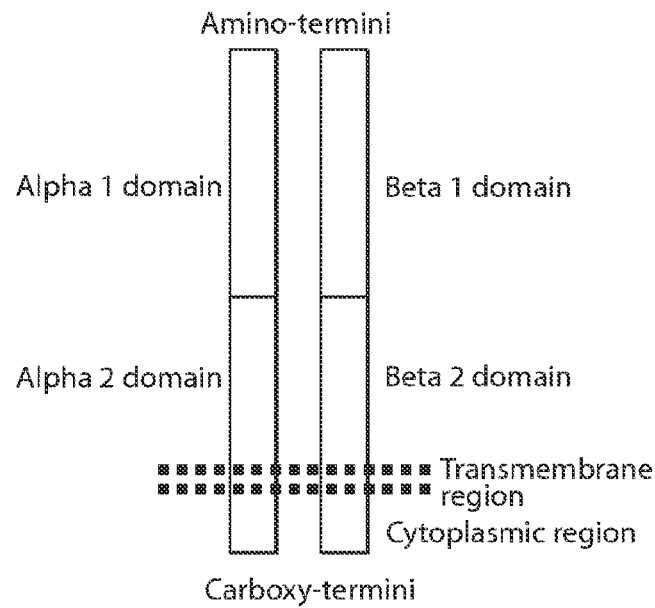
FIG. 4 is a schematic drawing depicting the structure of a class II molecule.

Class II molecules are normally found only on the surface of cells of the immune system. As shown in FIG. 4, class II protein molecules are heterodimers comprising a ca. 34 kDa polymorphic alpha chain and a ca. 28 kDa polymorphic beta chain. Approximately 0.5-1 million HLA class II molecules, including HLA-DR, HLA-DQ, and HLA-DP molecules, are expressed on the surface of any immune cell.

Each class II polypeptide chain includes two extracellular domains (each approximately 100 amino acids in length), a transmembrane domain, and a cytoplasmic tail. The amino-terminal extracellular domains are principally involved in antigen presentation, and the vast majority of class II polymorphism resides in this domain of one or both polypeptide chains. Each class II polypeptide chain is initially synthesized with a leader peptide on its amino terminus; this leader peptide is removed from the polypeptide chain during transport to the cell surface.

The genes or loci that encode the HLA-DR, -DQ, and -DP alpha (A) and beta (B) chains are located adjacent to one another in the major histocompatibility complex (MHC) on chromosome 6. See FIG. 2. The genes or loci that encode HLA-DR include HLA-DRA, HLA-DRB1, HLA-DRB3, HLA-DRB4, and HLA-DRB5. The DR molecule is comprised of an alpha polypeptide encoded by DRA and one beta polypeptide encoded by DRB1, DRB3, DRB4, or DRB5. Likewise, DQA1 and DQB1 encode a DQ molecule and DPA1 and DPB1 encode a DP molecule.

Each class II alpha chain locus and each class II beta chain locus includes both exons and introns. During transcription and translation, sequences corresponding to introns are removed, and exons are apposed to arrive at a coding sequence for the polypeptide product. The amino-terminal extracellular domain of each class II polypeptide is encoded by often polymorphic exon 2.

Each cell has both maternally and paternally inherited HLA-DR alleles, both maternally and paternally inherited HLA-DQ alleles, and both maternally and paternally inherited HLA-DP alleles. Because the genes encoding class II HLA molecules are co-dominant, each cell expresses HLA-DR molecules encoded by both maternally and paternally inherited HLA-DR alleles, HLA-DP molecules encoded by both maternally and paternally inherited HLA-DP alleles, and HLA-DQ molecules encoded by both maternally and paternally inherited HLA-DQ alleles. Some DQ and DP molecules may exist that combine maternally and paternally encoded polypeptide chains.

Most loci have many alleles. For example, the DRB1 locus has over 1300 alleles. Other loci have only a few alleles. For example, DRA has only seven alleles. Generally speaking, there is at most a 1 in 20,000 chance that any two individuals in a given ethnic group share the same HLA alleles. Some individuals may not find a match within the 22 million volunteers listed in world-wide registries.

The two alleles (maternal and paternal) carried by an individual for any given locus is called a genotype for that locus.

However, some copies of chromosome 6 carry only one expressed DR beta gene, while some copies of chromosome 6 carry two expressed DR beta genes. One expressed locus is DRB1, and the second expressed locus is DRB3, DRB4, or DRB5. Individuals who carry haplotypes (i.e., chromosomes) containing two DR loci express two different DR molecules encoded by that haplotype.

A problem with the existing methods of HLA typing relates to nomenclature of HLA alleles. This problem can be understood in terms of its historical roots and the more recent ability to specify alleles at a nucleotide sequence level.

The World Health Organization HLA Nomenclature Committee assigns names to alleles. Currently each HLA allele is designated by the name of the gene or locus followed by an asterisk and two to four fields separated by colons indicating the allele. For example, HLA-A*01:01:01:01 is an allele of the HLA-A gene; DPB1*02:01:02 is an allele of the HLA-DPB1 gene; DQB1*03:01:01:01 is an allele of the HLA-DQB1 gene; and DQA1*06:01:01 is an allele of the HLA-DQA1 gene. The first numbers in the numerical designation of each allele preceding the first colon are often based on the serologic type of the resultant protein and/or the similarity to other alleles in that group. The next field in the allele designation refers to the order in which the allele was discovered.

Alleles at the DRB1 locus include DRB1*01:01:01, DRB1*01:02:01, and DRB1*04:02:01. Sometimes shorter names are used, such as DRB1*01:01. This designation means that the typing does not distinguish among alleles whose names all start with DRB1*01:01; these include DRB1*01:01:01, DRB1*01:01:02, and DRB1*01:01:03.

Further complicating matters, hematopoietic progenitor cell donor registries may use letter codes to designate subsets of HLA alleles. For example, the letters AF in DRB1*14:AF mean *14:01 or *14:09, while DRB1*04:ABC means DRB1*04:03, *04:04, *04:06, *04:07, *04:08, *04:10, *04:11, *04:17, *04:19, *04:20, or *04:23.

Fields three and four in the allele name indicate DNA sequence variation that does not alter the resultant protein sequence (field 3) or variation outside of the coding exons (field 4). Differences at the DNA level can result in differences in the protein sequence or, due to degeneracy of the genetic code, can be silent at the protein level. Only silent changes are accorded numerical designations in the third field. Of course, such differences are effectively silent at the protein level as well. Variation in the fourth field can either have no impact on the protein sequence or may alter the level of expression of the protein.

Further, the designation optionally can end with the letter N to indicate a null or non-expressed allele. Other designations also exist, for example, S,Q. A description of HLA nomenclature can be found on a reference web site hla.alleles.org.

Low resolution HLA typing refers to a DNA-based typing result at the level of the digits composing the first field in the DNA-based nomenclature. Examples include A*01 and A*02. This resolution corresponds to a serologic antigen equivalent.

A high-resolution typing result is defined as a set of alleles that encode the same protein sequence for the region of the HLA molecule called the antigen recognition domain and that exclude alleles that are not expressed as cell-surface proteins. The antigen recognition domain includes domain 1 and domain 2 of the class I alpha polypeptides (encoded by exons 2 and 3), and domain 1 of the class II alpha and domain 1 of the class II beta polypeptide chains (both encoded by exon 2 of each gene).

If high resolution cannot be obtained or if the laboratory's agreement with the entity requesting the testing limits the typing efforts to a subset of alleles, the laboratory may report its results at a level of resolution that falls between high resolution and low resolution, i.e., intermediate resolution. Examples are to consider only those alleles expected to be found in the local population or that are designated as common and well defined. A third example is typing that assigns a G-group designation (e.g., A*02:01:01G).

HLA alleles that have identical nucleotide sequences across the exons encoding the antigen recognition domains (exon 2 and 3 for HLA class I and exon 2 only for HLA class II alleles), can be designated by the letter G which follows the first 3 fields of the allele designation of the lowest numbered allele in the group. The instant invention relates in part to the analysis and assignment of G-level HLA typing.

Methods of the Invention

An aspect of the invention is a method for human leukocyte antigen (HLA) typing, comprising the steps of performing one-step DNA sequencing of at least one HLA class I locus or at least one HLA class II locus of a subject, thereby providing at least intermediate resolution typing for the at least one HLA class I locus or the at least one HLA class II locus; performing sequence-specific probe hybridization for the at least one HLA class I locus or the at least one HLA class II locus, thereby providing a second at least intermediate resolution typing for the at least one HLA class I locus or the at least one HLA class II locus; and assigning, based on results of the one-step DNA sequencing and the sequence-specific probe hybridization, a single G-level genotype for the at least one HLA class I locus or the at least one HLA class II locus of the subject.

As a source of DNA, a sample of cells or a tissue is obtained from a subject. Human cells are collected from individuals or umbilical cord blood units using any of a variety of methods. These methods include, but are not restricted to, buccal swabbing, drawing blood into a tube containing acid citrate dextrose or other anti-coagulant, and by obtaining an aliquot of umbilical cord blood. For buccal swabbing, usually 4 buccal swabs are obtained, one from each quarter of the mouth. The cells or tissue sample are usually, but not necessarily, obtained from a living source of such cells or tissue. In certain embodiments, the cells or tissues can be obtained from a deceased subject, e.g., in a forensic application, or from a cell line.

Each sample is typically assigned a sample identification (ID), e.g., a random 1-D or 2-D bar code identifier. The sample ID can further include or otherwise be associated with additional sample information, e.g., the sample source. In one embodiment, the sample ID, sample source, and demographics are entered into Allelos software; the Allelos software records the date of entry and the identity of the individual entering the data. Individual sample IDs can be affixed to sample containers or otherwise associated with the physical location of each individual sample. For example, individual samples can be stored in individual tubes or aliquoted into individual wells of a multi-well plate. In the case of a multi-well plate, a map of the plate can be made to record the sample ID for each well. The map can take the form of a physical map or an electronic equivalent thereof, e.g., a table in an electronic spreadsheet. The sample ID can also be associated with any material and any step downstream of sample collection. In this way, sample ID follows the sample from its collection, to its analysis using DNA sequencing and probe hybridization, to its genotype assignment. This provides traceability of the sample.

Alternatively or in addition, unamplified genomic DNA isolated from a cell or tissue sample can be assigned a sample (ID), e.g., a random 1-D or 2-D bar code identifier.

Alternatively or in addition, amplified genomic DNA isolated from a cell or tissue sample can be assigned a sample (ID), e.g., a random 1-D or 2-D bar code identifier.

Genomic DNA is isolated from the cell or tissue sample. While any method for the extraction of genomic DNA can be used, in one embodiment, a Qiagen DNA extraction protocol/kit is used to isolate genomic DNA. DNA is extracted from one buccal swab, or an aliquot of blood or umbilical cord blood. The protocol is described, for example, in Examples 1, 2, and 3. In one embodiment, genomic DNA isolation is performed on a large number of individual samples, for example, using a robotic instrument suitable for such purpose. The extraction of one buccal swab or 200 µL of blood yields approximately 4-10 µg of genomic DNA. The isolated genomic DNA will include DNA of the major histocompatibility complex (MHC) genes known as HLA.

Isolated genomic DNA is optionally aliquoted and either used essentially right away for HLA typing or stored frozen for later use. For example, beginning with a single cell sample or tissue sample, genomic DNA isolated from the cell or tissue sample can be divided into aliquots for DNA amplification using polymerase chain reaction (PCR), DNA sequencing, probe hybridization, and/or storage.

In one embodiment, desired exons of specific HLA class I genes are amplified from isolated genomic DNA using PCR with a first set of PCR oligonucleotide primers, thereby generating amplicons for use in DNA sequencing, and, in parallel, desired exons of specific HLA class I genes are amplified from isolated genomic DNA using PCR with a second set of PCR oligonucleotide primers, thereby generating amplicons for use in probe hybridization.

In one embodiment, desired exons of specific HLA class I genes are amplified from isolated genomic DNA using PCR with a first set of PCR oligonucleotide primers, thereby generating amplicons for use in DNA sequencing, and, in series, desired exons of specific HLA class I genes are amplified from isolated genomic DNA using PCR with a second set of PCR oligonucleotide primers, thereby generating amplicons for use in probe hybridization.

In one embodiment, desired exons of specific HLA class I genes are amplified from isolated genomic DNA using a single locus-specific PCR amplification before the sample is divided for sequencing and probe hybridization, thereby generating amplicons for use both in DNA sequencing and in probe hybridization.

In accordance with each of the foregoing, in one embodiment, class II typing is performed solely by probe hybridization.

In accordance with each of the foregoing, in one embodiment, class II typing is performed solely by PCR amplification followed by probe hybridization.

Alternatively, in accordance with each of the foregoing, in one embodiment, class II typing is performed using a joint sequencing and hybridization approach similar to that used for class I.

Amplification of HLA Genes Using the Polymerase Chain Reaction for DNA Sequencing An aliquot of genomic DNA (e.g., approximately 5 µL from Qiagen preparation) is incubated with HLA-A, -B, or -C locus-specific primers in a polymerase chain reaction.

PCR primers and primer pairs are described in Examples 14 and 16, and an amplification protocol is described in Example 5. Following amplification, excess primers and nucleotides (dNTP) are removed, e.g., using Agencourt AMPure (Beckman Coulter, Inc.) and the amplification may be quantified. See, for example, Examples 5, 9, and 10.

The polymerase chain reaction is a well-known and widely used technique to amplify a target sequence of DNA. In 1993, Kary Mullis and Michael Smith were awarded the Nobel Prize in Chemistry for their work on PCR. The method is described, for example, in U.S. Pat. No. 4,683, 202, the contents of which are incorporated herein by reference.

The method relies on thermal cycling, consisting of cycles of repeated heating and cooling of the reaction for DNA melting and enzymatic replication of the DNA. Primers (short DNA fragments) containing sequences complementary to the target region along with a DNA polymerase (after which the method is named) are key components to enable selective and repeated amplification. As PCR progresses, the DNA generated is itself used as a template for replication, setting in motion a chain reaction in which the DNA template is exponentially amplified.

Almost all PCR applications employ a heat-stable DNA polymerase, such as Taq polymerase, an enzyme originally isolated from the bacterium *Thermus aquaticus*. This DNA polymerase enzymatically assembles a new DNA strand from DNA building-blocks, i.e., deoxynucleotides, by using single-stranded DNA as a template and DNA oligonucleotides (primers), which are required for initiation of DNA synthesis. The vast majority of PCR methods use thermal cycling, i.e., alternately heating and cooling the PCR sample through a defined series of temperature steps. In the first step, the two strands of the DNA double helix are physically separated at a high temperature in a process called DNA melting. In the second step, the temperature is lowered and the primers anneal to the separate strands. In a third step the temperature is raised to an intermediate temperature and the two DNA strands serve as templates for DNA polymerase to extend the primers and selectively amplify the target DNA. The selectivity of PCR results from the use of primers that are complementary to the DNA region targeted for amplification under specific thermal cycling conditions.

In the context of the present invention, the template DNA generally is genomic DNA comprising DNA of the MHC. Notably, it is not necessary to separate alleles for use in DNA amplification, DNA sequencing, or probe hybridization.

In preparation for subsequent DNA sequencing, PCR amplification will typically employ oligonucleotide primers having sequences which are capable of hybridizing, in one embodiment, to intronic regions flanking one or more class I exons of interest. For example, PCR primers for HLA-A can comprise pairs of primers selected to amplify exon 2, exon 3, or both exon 2 and exon 3 of HLA-A. Similarly, PCR primers for HLA-B can comprise pairs of primers selected to amplify exon 2, exon 3, or both exon 2 and exon 3 of HLA-B. Likewise, PCR primers for HLA-C can comprise pairs of primers selected to amplify exon 2, exon 3, or both exon 2 and exon 3 of HLA-C.

In certain embodiments, oligonucleotide primers are selected to have sequences which are capable of hybridizing with at least part of one or more class I exons of interest. For example, PCR primers for HLA-A can comprise pairs of primers selected to amplify at least part of exon 2, at least part of exon 3, at least part of exon 2 and at least part of exon 3, at least part of exon 2 and essentially all of exon 3, essentially all of exon 2 and at least part of exon 3, or essentially all of exon 2 and essentially all of exon 3 of HLA-A. Similarly, PCR primers for HLA-B can comprise pairs of primers selected to amplify at least part of exon 2, at least part of exon 3, at least part of exon 2 and at least part of exon 3, at least part of exon 2 and essentially all of exon 3, essentially all of exon 2 and at least part of exon 3, or essentially all of exon 2 and essentially all of exon 3 of HLA-B. Likewise, PCR primers for HLA-C can comprise pairs of primers selected to amplify at least part of exon 2, at least part of exon 3, at least part of exon 2 and at least part of exon 3, at least part of exon 2 and essentially all of exon 3, essentially all of exon 2 and at least part of exon 3, or essentially all of exon 2 and essentially all of exon 3 of HLA-C.

In preparation for subsequent DNA sequencing, PCR amplification will typically employ oligonucleotide primers having sequences which are capable of hybridizing, in one embodiment, to intronic regions flanking one or more class II exons of interest. For example, PCR primers for HLA-DRB1 can comprise pairs of primers selected to amplify exon 2 of HLA-DRB1. Similarly, PCR primers for HLA-DQB1 can comprise pairs of primers selected to amplify exon 2 HLA-DQB1. Likewise, PCR primers for HLA-DPB1 can comprise pairs of primers selected to amplify exon 2 of HLA-DQB1.

In certain embodiments, oligonucleotide primers are selected to have sequences which are capable of hybridizing with at least part of one or more class II exons of interest. For example, PCR primers for HLA-DRB1 can comprise pairs of primers selected to amplify at least part of exon 2 of HLA-DRB1. Similarly, PCR primers for HLA-DQB1 can comprise pairs of primers selected to amplify at least part of exon 2 of HLA-DQB1. Likewise, PCR primers for HLA-DPB1 can comprise pairs of primers selected to amplify at least part of exon 2 of HLA-DPB1. In one embodiment, PCR primers for HLA-DRB1 comprise pairs of primers selected to amplify at least essentially all of exon 2 of HLA-DRB1. Similarly, in one embodiment PCR primers for HLA-DQB1 comprise pairs of primers selected to amplify essentially all of exon 2 of HLA-DQB1. Likewise, in one embodiment PCR primers for HLA-DPB1 comprise pairs of primers selected to amplify essentially all of exon 2 of HLA-DPB1.

Alternatively or in addition, in certain embodiments, oligonucleotide primers are selected to have sequences which are capable of hybridizing with at least part of one or more introns adjacent to one or more class II exons of interest.

In one embodiment, locus-specific primers, annealing in the introns 5' of exon 2 and 3' of exon 3 are used to amplify both alleles at a given class I locus.

In one embodiment, locus-specific primers, annealing in the introns 5' and 3' of exon 2 are used to amplify both alleles at a given class II locus.

Oligonucleotide primers for use in PCR amplification can be made using conventional techniques and starting materials, including use of commercially available programmable oligonucleotide synthesizers. In certain embodiments, an oligonucleotide primer for use in PCR amplification comprise a detectable tag or marker, such as a fluorescent tag or marker, usually incorporated at or attached to the 5' end of the oligonucleotide. In one embodiment, the detectable tag or marker is biotin.

PCR amplification can be conveniently performed using commercially available programmable thermal cyclers. Such devices typically accommodate 48, 96, or 384 samples at a time. The set-up for the PCR amplification reactions can be partially or fully facilitated using a robotic multichannel automation station, e.g., a Biomek multichannel automation workstation (Beckman Coulter, Brea, Calif.) or Bravo multichannel automation workstation (Velocity 11, Menlo Park, Calif.).

An exemplary program for PCR amplification of HLA-A and -B loci is as follows (see Example 5):
1. 94° C. for 2 min
2. 8 cycles:
  94° C. for 22 sec
  65° C. for 50 sec
  72° C. for 30 sec
3. 30 cycles:
  94° C. for 22 sec
  62° C. for 50 sec
  72° C. for 30 sec
4. 72° C. for 10 min
5. 4° C. hold Following completion of PCR amplification, PCR products (amplicons) can optionally be confirmed and quantified using standard agarose gel electrophoresis or by measuring optical density (Example 10), and they can be cleaned up (purified) by removing unincorporated primers and nucleotides.

As indicated above, a feature of the invention is the use of one-step DNA sequencing (also referred to as one-pass DNA sequencing) of at least one HLA class I locus or at least one HLA class II locus. In one embodiment, this feature involves DNA sequencing focused on exons 2 and 3 of class I genes without separation of alleles and without secondary PCR amplifications or sequencing reactions. In one embodiment, this feature involves DNA sequencing focused on exon 2 of class II antigens without separation of alleles and without secondary PCR amplifications or sequencing reactions. Advantageously, the elimination of secondary assays such as PCR amplifications reduces costs and errors.

The protocol is established for the use of Sanger sequencing. In one embodiment, Class I and II DNA amplicons carrying the exons of interest are sequenced using oligonucleotide primers that anneal in introns flanking each exon (Example 5). In one embodiment, each exon of interest is sequenced in both directions, i.e., both the sense strand and the antisense strand are sequenced; of course this involves the use of two sequencing reactions and two sequencing primers (forward and reverse) for any given exon. Following the sequencing reaction, the amplicon is purified, e.g., using Agencourt AMPure (Beckman Coulter, Inc.), removing unincorporated primers and nucleotides (see Example 6 and Example 9). The DNA fragments are electrophoresed on a DNA analyzer, e.g., an Applied Biosystems 3730xL DNA Analyzer. Software for the DNA analyzer, e.g., the Applied Biosystems analysis software from the 3730xL DNA Analyzer, converts the fluorescent values from Sanger sequencing into a DNA sequence.

Sequencing primers and primer pairs include those listed in Examples 15 and 17. These primers may anneal in introns or partially in intron/exon or in the exon.

The one-step DNA sequencing provides at least intermediate resolution typing for the at least one exon of interest. Taken together, the one-step DNA sequencing provides at least intermediate resolution typing for exons 2 and 3 of a class I locus; i.e., the one-step DNA sequencing provides at least intermediate resolution typing of a class I locus. Alternatively or in addition, the one-step DNA sequencing provides at least intermediate resolution typing for exon 2 of a class II locus; i.e., the one-step DNA sequencing provides at least intermediate resolution typing of a class II locus.

In one embodiment, the sequence information is collected and processed by Assign ATF software of the invention.

This software is a modification of commercially available software from Conexio Genomics (conexio-genomics.com). It was modified by Conexio under a contract to Georgetown University and with the present inventors' input. This software assembles individual nucleotide sequences into a contiguous sequence and compares that assembled sequence to a database of reference HLA sequences. It provides a list of HLA genotypes compatible with the sequence. It provides a report with the sequence(s) and the assignment(s).

Amplification of HLA Genes Using the Polymerase Chain Reaction for Hybridization The sequence information obtained using one-step DNA sequencing just described can be complemented by sequence-specific oligonucleotide probe (SSOP) hybridization information. The hybridization can be used to arrive at a higher level resolution for any given locus. The hybridization can be used to resolve any ambiguities arising from the sequencing alone by determining the phase of polymorphisms.

In one embodiment, class II typing is performed by probe hybridization alone.

In one embodiment, class II typing is performed PCR amplification followed by probe hybridization alone.

An aliquot of genomic DNA (e.g., approximately 2 µL from Qiagen preparation) is incubated with either HLA-A, -B, -C locus-specific primers in a polymerase chain reaction. Two pairs of primers, one for exon 2 and one for exon 3, are used to amplify the DNA in a multiplex reaction. In one embodiment, the reagents are provided in a One Lambda LABType Kit (see Example 4). In one embodiment, the reagents are provided in a modified version of a One Lambda LABType Kit. One primer in each pair is tagged with biotin to enable detection in the subsequent Luminex assay.

A similar strategy is used to identify class II alleles.

Sequence-Specific Oligonucleotide Hybridization Using One Lambda LABType HD Kit

This kit, developed by One Lambda (onelambda.com), is based on solid phase reverse sequence-specific oligonucleotide probe (rSSOP) hybridization using microspheres as a solid support to immobilize oligonucleotide probes. The PCR-amplified target DNA is hybridized with the bead-bound probe array. Binding of genomic DNA to each probe is measured by addition of a fluorescently tagged avidin-containing detection reagent that detects biotin incorporated into the PCR oligonucleotide primers. Detection of binding and bead identity is measured using a Luminex system (luminexcorp.com). One Lambda Fusion Software is used to collect, analyze, and interpret the hybridization results into HLA assignments based on a current version of the IMmunoGeneTics (IMGT)/HLA database (ebi.ac.uk/ipdlimgt/hla). In one embodiment, the results are reviewed by laboratory personnel. The protocol is further described in Example 11, Example 12, and Example 13.

In one embodiment, oligonucleotide probes that are part of the One Lambda LABType kit will be used. In one embodiment, the oligonucleotide reagents are modified to meet resolution standards of the invention. New reagents will also be designed based on information about new alleles. The sequences of the oligonucleotide probes are selected to meet several criteria:
1. Hybridize to polymorphic sequences of HLA alleles chosen to discriminate among HLA alleles.

2. Include oligonucleotides designed to bridge two polymorphic regions with the goal of determining nucleotide phase.

3. Hybridize in a robust and consistent fashion with HLA genes with a clear and consistent distinction between lack of hybridization and hybridization.

The results of the one-step DNA sequencing and the sequence-specific oligonucleotide probe hybridization are used together to arrive at and assign a single HLA genotype for the at least one HLA class I locus or the at least one HLA class II locus of the subject. In addition, the results of the one-step DNA sequencing and the sequence-specific oligonucleotide probe hybridization are used together to arrive at a partial DNA sequence for each allele of the at least one HLA class I locus or the at least one HLA class II locus of the subject.

Results of the method can include identification of HLA genotypes for potential donors and recipients. Such information obtained using any aspect of the invention can be submitted to a hematopoietic progenitor cell (e.g., bone marrow) donor, umbilical cord blood or other tissue or organ donor registry, or provided to a physician. Information can also be submitted to research databases.

Results of the method can include identification of novel alleles. Information about novel alleles identified using any aspect of the invention can be submitted to an HLA database.

In one embodiment, the at least one HLA class I locus is selected from the group consisting of HLA-A, HLA-B, and HLA-C.

In one embodiment, the at least one HLA class I locus comprises HLA-A.

In one embodiment, the at least one HLA class I locus comprises HLA-B.

In one embodiment, the at least one HLA class I locus comprises HLA-C.

In one embodiment, the at least one HLA class I locus comprises HLA-A and HLA-B.

In one embodiment, the at least one HLA class I locus comprises HLA-A and HLA-C.

In one embodiment, the at least one HLA class I locus comprises HLA-B and HLA-C.

In one embodiment, the at least one HLA class I locus comprises HLA-A, HLA-B, and HLA-C.

In one embodiment, the at least one HLA class I locus is HLA-A.

In one embodiment, the at least one HLA class I locus is HLA-B.

In one embodiment, the at least one HLA class I locus is HLA-C.

In one embodiment, the at least one HLA class I locus is HLA-A and HLA-B.

In one embodiment, the at least one HLA class I locus is HLA-A and HLA-C.

In one embodiment, the at least one HLA class I locus is HLA-B and HLA-C.

In one embodiment, the at least one HLA class I locus is HLA-A, HLA-B, and HLA-C.

In one embodiment, the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class II locus comprises HLA-DRB1.

In one embodiment, the at least one HLA class II locus comprises HLA-DRB3.

In one embodiment, the at least one HLA class II locus comprises HLA-DRB4.

In one embodiment, the at least one HLA class II locus comprises HLA-DRB5.

In one embodiment, the at least one HLA class II locus comprises HLA-DQA1.

In one embodiment, the at least one HLA class II locus comprises HLA-DPA1.

In one embodiment, the at least one HLA class II locus comprises HLA-DQB1.

In one embodiment, the at least one HLA class II locus comprises HLA-DPB1.

In one embodiment, the at least one HLA class II locus is HLA-DRB1.

In one embodiment, the at least one HLA class II locus is HLA-DRB3.

In one embodiment, the at least one HLA class II locus is HLA-DRB4.

In one embodiment, the at least one HLA class II locus is HLA-DRB5.

In one embodiment, the at least one HLA class II locus is HLA-DQA1.

In one embodiment, the at least one HLA class II locus is HLA-DPA1.

In one embodiment, the at least one HLA class II locus is HLA-DQB1.

In one embodiment, the at least one HLA class II locus is HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DQB1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus is selected from the group consisting of HLA-DRB1, HLA-DQB1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus comprises HLA-DRB1, HLA-DQB1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus comprises HLA-DRB1, HLA-DQB1, and HLA-DPB1.

In one embodiment, the at least one HLA class I locus comprises HLA-A and HLA-B, and the at least one HLA class II locus comprises HLA-DRB1.

In one embodiment, the at least one HLA class I locus comprises HLA-A and HLA-B, and the at least one HLA class II locus is HLA-DRB1.

An aspect of the invention is a method for human leukocyte antigen (HLA) typing, comprising amplifying DNA encoding at least one HLA class I locus or at least one HLA class II locus of a subject, thereby providing an amplicon of the at least one HLA class I locus or the at least one HLA class II locus of the subject; performing one-step DNA sequencing of the amplicon of the at least one HLA class I locus or the at least one HLA class II locus of the subject, thereby providing a first at least intermediate resolution typing for the at least one HLA class I locus or the at least one HLA class II locus; performing sequence-specific probe hybridization of the amplicon of the at least one HLA class I locus or the at least one HLA class II locus of the subject, thereby providing a second at least intermediate resolution typing for the at least one HLA class I locus or the at least one HLA class II locus; and assigning, based on results of the one-step DNA sequencing and the sequence-specific probe hybridization, a single G-level genotype for the at least one HLA class I locus or the at least one HLA class II locus of the subject.

In one embodiment, the amplifying DNA encoding at least one HLA class I locus or at least one HLA class II locus of a subject comprises using a first set of oligonucleotide primers having nucleotide sequences selected from the group consisting of SEQ ID NOs 1-29. In one embodiment, the performing one-step DNA sequencing of the amplicon of the at least one HLA class I locus or the at least one HLA class II locus of the subject comprises using a second set of oligonucleotide primers having nucleotide sequences selected from the group consisting of SEQ ID NOs 4 and 30-54. In one embodiment, the amplifying DNA encoding at least one HLA class I locus or at least one HLA class II locus of a subject comprises using a first set of oligonucleotide primers having nucleotide sequences selected from the group consisting of SEQ ID NOs 1-29, and the performing one-step DNA sequencing of the amplicon of the at least one HLA class I locus or the at least one HLA class II locus of the subject comprises using a second set of oligonucleotide primers having nucleotide sequences selected from the group consisting of SEQ ID NOs 4 and 30-54.

In one embodiment, the amplifying DNA encoding at least one HLA class I locus comprises amplifying an exon selected from the group consisting of exon 2 and exon 3 of the at least one HLA class I locus.

In one embodiment, the amplifying DNA encoding at least one HLA class I locus comprises using a first pair of oligonucleotide primers for exon 2 and a second pair of oligonucleotide primers for exon 3 of the at least one HLA class I locus. For example, the first pair of oligonucleotide primers may anneal to intron sequences flanking exon 2, while the second pair of oligonucleotide primers may anneal to intron sequences flanking exon 3.

In one embodiment, the amplifying DNA encoding at least one HLA class I locus comprises amplifying exon 2 and exon 3 of the at least one HLA class I locus.

In one embodiment, the amplifying DNA encoding at least one HLA class I locus comprising amplifying exon 2 and exon 3 of the at least one HLA class I locus comprises using a first oligonucleotide primer that anneals to an intron sequence 5' of exon 2, and a second oligonucleotide primer that anneals to an intron sequence 3' of exon 3.

In one embodiment, the amplifying DNA encoding at least one HLA class I locus comprises a first amplification for use in performing the one-step DNA sequencing and a second amplification for use in performing the sequence-specific probe hybridization. Each amplification produces an amplicon. The first amplification produces a first amplicon for use in performing the one-step DNA sequencing. The second amplification produces a second amplicon for use in performing the sequence-specific probe hybridization. The first and second amplifications typically use first and second pairs of oligonucleotide primers, respectively.

In one embodiment, the amplifying DNA encoding at least one HLA class II locus comprises amplifying exon 2 of the alpha gene of the at least one HLA class II locus.

In one embodiment, the amplifying DNA encoding at least one HLA class II locus comprises amplifying exon 2 of the beta gene of the at least one HLA class II locus.

In one embodiment, the amplifying DNA encoding at least one HLA class I locus comprising amplifying exon 2 of the alpha gene of the at least one HLA class II locus comprises using a pair of oligonucleotide primers that anneal to intron sequences flanking exon 2 of the alpha gene of the at least one HLA class II locus.

In one embodiment, the amplifying DNA encoding at least one HLA class I locus comprising amplifying exon 2 of the beta gene of the at least one HLA class II locus comprises using a pair of oligonucleotide primers that anneal to intron sequences flanking exon 2 of the beta gene of the at least one HLA class II locus.

In one embodiment, the amplifying DNA encoding at least one HLA class II locus comprises a first amplification for use in performing the one-step DNA sequencing and a second amplification for use in performing the sequence-specific probe hybridization. Each amplification produces an amplicon. The first amplification produces a first amplicon for use in performing the one-step DNA sequencing. The second amplification produces a second amplicon for use in performing the sequence-specific probe hybridization. The first and second amplifications typically use first and second pairs of oligonucleotide primers, respectively.

In one embodiment, the at least one HLA class I locus is selected from the group consisting of HLA-A, HLA-B, and HLA-C.

In one embodiment, the at least one HLA class I locus comprises HLA-A.

In one embodiment, the at least one HLA class I locus comprises HLA-B.

In one embodiment, the at least one HLA class I locus comprises HLA-C.

In one embodiment, the at least one HLA class I locus comprises HLA-A and HLA-B.

In one embodiment, the at least one HLA class I locus comprises HLA-A and HLA-C.

In one embodiment, the at least one HLA class I locus comprises HLA-B and HLA-C.

In one embodiment, the at least one HLA class I locus comprises HLA-A, HLA-B, and HLA-C.

In one embodiment, the at least one HLA class I locus is HLA-A.

In one embodiment, the at least one HLA class I locus is HLA-B.

In one embodiment, the at least one HLA class I locus is HLA-C.

In one embodiment, the at least one HLA class I locus is HLA-A and HLA-B.

In one embodiment, the at least one HLA class I locus is HLA-A and HLA-C.

In one embodiment, the at least one HLA class I locus is HLA-B and HLA-C.

In one embodiment, the at least one HLA class I locus is HLA-A, HLA-B, and HLA-C.

In one embodiment, the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class II locus comprises HLA-DRB1.

In one embodiment, the at least one HLA class II locus comprises HLA-DRB3.

In one embodiment, the at least one HLA class II locus comprises HLA-DRB4.

In one embodiment, the at least one HLA class II locus comprises HLA-DRB5.

In one embodiment, the at least one HLA class II locus comprises HLA-DQA1.

In one embodiment, the at least one HLA class II locus comprises HLA-DPA1.

In one embodiment, the at least one HLA class II locus comprises HLA-DQB1.

In one embodiment, the at least one HLA class II locus comprises HLA-DPB1.

In one embodiment, the at least one HLA class II locus is HLA-DRB1.

In one embodiment, the at least one HLA class II locus is HLA-DRB3.

In one embodiment, the at least one HLA class II locus is HLA-DRB4.

In one embodiment, the at least one HLA class II locus is HLA-DRB5.

In one embodiment, the at least one HLA class II locus is HLA-DQA1.

In one embodiment, the at least one HLA class II locus is HLA-DPA1.

In one embodiment, the at least one HLA class II locus is HLA-DQB1.

In one embodiment, the at least one HLA class II locus is HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DQB1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus is selected from the group consisting of HLA-DRB1, HLA-DQB1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus comprises HLA-DRB1, HLA-DQB1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus comprises HLA-DRB1, HLA-DQB1, and HLA-DPB1.

In one embodiment, the at least one HLA class I locus comprises HLA-A and HLA-B, and the at least one HLA class II locus comprises HLA-DRB1.

In one embodiment, the at least one HLA class I locus comprises HLA-A and HLA-B, and the at least one HLA class II locus is HLA-DRB1.

An aspect of the invention is a method for human leukocyte antigen (HLA) typing, comprising performing one-step DNA sequencing of at least one HLA class I locus and at least one HLA class II locus of a subject, thereby providing a first at least intermediate resolution typing for the at least one HLA class I locus and the at least one HLA class II locus; performing sequence-specific probe hybridization for the at least one HLA class I locus and the at least one HLA class II locus, thereby providing a second at least intermediate resolution typing for the at least one HLA class I locus and the at least one HLA class II locus; and assigning, based on results of the one-step DNA sequencing and the sequence-specific probe hybridization, a single G-level genotype for the at least one HLA class I locus and the at least one HLA class II locus of the subject.

In one embodiment, the at least one HLA class I locus is selected from the group consisting of HLA-A, HLA-B, and HLA-C.

In one embodiment, the at least one HLA class I locus comprises HLA-A.

In one embodiment, the at least one HLA class I locus comprises HLA-B.

In one embodiment, the at least one HLA class I locus comprises HLA-C.

In one embodiment, the at least one HLA class I locus comprises HLA-A and HLA-B.

In one embodiment, the at least one HLA class I locus comprises HLA-A and HLA-C.

In one embodiment, the at least one HLA class I locus comprises HLA-B and HLA-C.

In one embodiment, the at least one HLA class I locus comprises HLA-A, HLA-B, and HLA-C.

In one embodiment, the at least one HLA class I locus is HLA-A.

In one embodiment, the at least one HLA class I locus is HLA-B.

In one embodiment, the at least one HLA class I locus is HLA-C.

In one embodiment, the at least one HLA class I locus is HLA-A and HLA-B.

In one embodiment, the at least one HLA class I locus is HLA-A and HLA-C.

In one embodiment, the at least one HLA class I locus is HLA-B and HLA-C.

In one embodiment, the at least one HLA class I locus is HLA-A, HLA-B, and HLA-C.

In one embodiment, the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class II locus comprises HLA-DRB1.

In one embodiment, the at least one HLA class II locus comprises HLA-DRB3.

In one embodiment, the at least one HLA class II locus comprises HLA-DRB4.

In one embodiment, the at least one HLA class II locus comprises HLA-DRB5.

In one embodiment, the at least one HLA class II locus comprises HLA-DQA1.

In one embodiment, the at least one HLA class II locus comprises HLA-DPA1.

In one embodiment, the at least one HLA class II locus comprises HLA-DQB1.

In one embodiment, the at least one HLA class II locus comprises HLA-DPB1.

In one embodiment, the at least one HLA class II locus is HLA-DRB1.

In one embodiment, the at least one HLA class II locus is HLA-DRB3.

In one embodiment, the at least one HLA class II locus is HLA-DRB4.

In one embodiment, the at least one HLA class II locus is HLA-DRB5.

In one embodiment, the at least one HLA class II locus is HLA-DQA1.

In one embodiment, the at least one HLA class II locus is HLA-DPA1.

In one embodiment, the at least one HLA class II locus is HLA-DQB1.

In one embodiment, the at least one HLA class II locus is HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DQB1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus is selected from the group consisting of HLA-DRB1, HLA-DQB1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus comprises HLA-DRB1, HLA-DQB1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus comprises HLA-DRB1, HLA-DQB1, and HLA-DPB1.

In one embodiment, the at least one HLA class I locus comprises HLA-A and HLA-B, and the at least one HLA class II locus comprises HLA-DRB1.

In one embodiment, the at least one HLA class I locus comprises HLA-A and HLA-B, and the at least one HLA class II locus is HLA-DRB1.

An aspect of the invention is a method for human leukocyte antigen (HLA) typing, comprising amplifying DNA encoding at least one HLA class I locus and at least one HLA class II locus of a subject, thereby providing an amplicon of the at least one HLA class I locus and an amplicon of the at least one HLA class II locus of the subject; performing one-step DNA sequencing of the amplicon of the at least one HLA class I locus and the amplicon of the at least one HLA class II locus of the subject, thereby providing a first at least intermediate resolution typing for the at least one HLA class I locus and the at least one HLA class II locus; performing sequence-specific probe hybridization of the amplicon of the at least one HLA class I locus and the amplicon of the at least one HLA class II locus of the subject, thereby providing a second at least intermediate resolution typing for the at least one HLA class I locus and the at least one HLA class II locus; and assigning, based on results of the one-step DNA sequencing and the sequence-specific probe hybridization, a single G-level genotype for the at least one HLA class I locus and the at least one HLA class II locus of the subject.

In one embodiment, the amplifying DNA encoding at least one HLA class I locus or at least one HLA class II locus of a subject comprises using a first set of oligonucleotide primers having nucleotide sequences selected from the group consisting of SEQ ID NOs 1-29. In one embodiment, the performing one-step DNA sequencing of the amplicon of the at least one HLA class I locus or the at least one HLA class II locus of the subject comprises using a second set of oligonucleotide primers having nucleotide sequences selected from the group consisting of SEQ ID NOs 4 and 30-54. In one embodiment, the amplifying DNA encoding at least one HLA class I locus or at least one HLA class II locus of a subject comprises using a first set of oligonucleotide primers having nucleotide sequences selected from the group consisting of SEQ ID NOs 1-29, and the performing one-step DNA sequencing of the amplicon of the at least one HLA class I locus or the at least one HLA class II locus of the subject comprises using a second set of oligonucleotide primers having nucleotide sequences selected from the group consisting of SEQ ID NOs 4 and 30-54.

In one embodiment, the amplifying DNA encoding at least one HLA class I locus comprises amplifying an exon selected from the group consisting of exon 2 and exon 3 of the at least one HLA class I locus.

In one embodiment, the amplifying DNA encoding at least one HLA class I locus comprises using a first pair of oligonucleotide primers for exon 2 and a second pair of oligonucleotide primers for exon 3 of the at least one HLA class I locus. For example, the first pair of oligonucleotide primers may anneal to intron sequences flanking exon 2, while the second pair of oligonucleotide primers may anneal to intron sequences flanking exon 3.

In one embodiment, the amplifying DNA encoding at least one HLA class I locus comprises amplifying exon 2 and exon 3 of the at least one HLA class I locus.

In one embodiment, the amplifying DNA encoding at least one HLA class I locus comprising amplifying exon 2 and exon 3 of the at least one HLA class I locus comprises using a first oligonucleotide primer that anneals to an intron sequence 5' of exon 2, and a second oligonucleotide primer that anneals to an intron sequence 3' of exon 3.

In one embodiment, the amplifying DNA encoding at least one HLA class I locus comprises using a first oligonucleotide primer for exon 2 and a second oligonucleotide primer for exon 3 of the at least one HLA class I locus, thereby generating a single amplicon comprising exon 2 and exon 3 of the at least one HLA class I locus.

As used herein, an "oligonucleotide primer for exon 2" refers to an oligonucleotide comprising a nucleotide sequence suitable for hybridizing to sequence within, flanking, or both within and flanking exon 2. In one embodiment, an "oligonucleotide primer for exon 2" refers to an oligonucleotide comprising a nucleotide sequence suitable for hybridizing to intronic sequence flanking exon 2. In one embodiment, an "oligonucleotide primer for exon 2" refers to an oligonucleotide comprising a nucleotide sequence suitable for hybridizing to flanking intronic sequence 5' to exon 2.

As used herein, an "oligonucleotide primer for exon 3" refers to an oligonucleotide comprising a nucleotide sequence suitable for hybridizing to sequence within, flanking, or both within and flanking exon 3. In one embodiment, an "oligonucleotide primer for exon 3" refers to an oligonucleotide comprising a nucleotide sequence suitable for hybridizing to intronic sequence flanking exon 3. In one embodiment, an "oligonucleotide primer for exon 3" refers to an oligonucleotide comprising a nucleotide sequence suitable for hybridizing to flanking intronic sequence 3' to exon 3.

As used herein, a "single amplicon comprising exon 2 and exon 3 of the at least one HLA class I locus" refers to a single, contiguous, amplified nucleotide sequence that includes essentially all of exon 2 and essentially all of exon 3 of the at least one HLA class I locus. In one embodiment, a "single amplicon comprising exon 2 and exon 3 of the at least one HLA class I locus" refers to a single, contiguous, amplified nucleotide sequence that includes all of exon 2 and essentially all of exon 3 of the at least one HLA class I locus. In one embodiment, a "single amplicon comprising exon 2 and exon 3 of the at least one HLA class I locus" refers to a single, contiguous, amplified nucleotide sequence that includes essentially all of exon 2 and all of exon 3 of the at least one HLA class I locus. In one embodiment, a "single amplicon comprising exon 2 and exon 3 of the at least one HLA class I locus" refers to a single, contiguous, amplified nucleotide sequence that includes all of exon 2 and all of exon 3 of the at least one HLA class I locus.

In each of the foregoing embodiments, the single, contiguous, amplified nucleotide sequence can, in certain embodiments, further include at least one nucleotide of an intron flanking exon 2, at least one nucleotide of an intron flanking exon 3, or at least one nucleotide of an intron flanking exon 2 and at least one nucleotide of an intron flanking exon 3. In each of the foregoing embodiments, the single, contiguous, amplified nucleotide sequence can, in certain embodiments, further include at least one nucleotide of a flanking intron 5' to exon 2, at least one nucleotide of a flanking intron 3' to exon 3, or at least one nucleotide of a flanking intron 5' to exon 2 and at least one nucleotide of a flanking intron 3' to exon 3.

In one embodiment, the amplifying DNA encoding at least one HLA class I locus comprises a first amplification for use in performing the one-step DNA sequencing and a second amplification for use in performing the sequence-specific probe hybridization. Each amplification produces an amplicon. The first amplification produces a first amplicon for use in performing the one-step DNA sequencing. The second amplification produces a second amplicon for use in performing the sequence-specific probe hybridization. The first and second amplifications typically use first and second pairs of oligonucleotide primers, respectively.

In one embodiment, the amplifying DNA encoding at least one HLA class II locus comprises amplifying exon 2 of the alpha gene of the at least one HLA class II locus.

In one embodiment, the amplifying DNA encoding at least one HLA class II locus comprises amplifying exon 2 of the beta gene of the at least one HLA class II locus.

In one embodiment, the amplifying DNA encoding at least one HLA class I locus comprising amplifying exon 2 of the alpha gene of the at least one HLA class II locus comprises using a pair of oligonucleotide primers that anneal to intron sequences flanking exon 2 of the alpha gene of the at least one HLA class II locus.

In one embodiment, the amplifying DNA encoding at least one HLA class I locus comprising amplifying exon 2 of the beta gene of the at least one HLA class II locus comprises using a pair of oligonucleotide primers that anneal to intron sequences flanking exon 2 of the beta gene of the at least one HLA class II locus.

In one embodiment, the amplifying DNA encoding at least one HLA class II locus comprises a first amplification for use in performing the one-step DNA sequencing and a second amplification for use in performing the sequence-specific probe hybridization. Each amplification produces an amplicon. The first amplification produces a first amplicon for use in performing the one-step DNA sequencing. The second amplification produces a second amplicon for use in performing the sequence-specific probe hybridization. The first and second amplifications typically use first and second pairs of oligonucleotide primers, respectively.

In one embodiment, the at least one HLA class I locus is selected from the group consisting of HLA-A, HLA-B, and HLA-C.

In one embodiment, the at least one HLA class I locus comprises HLA-A.

In one embodiment, the at least one HLA class I locus comprises HLA-B.

In one embodiment, the at least one HLA class I locus comprises HLA-C.

In one embodiment, the at least one HLA class I locus comprises HLA-A and HLA-B.

In one embodiment, the at least one HLA class I locus comprises HLA-A and HLA-C.

In one embodiment, the at least one HLA class I locus comprises HLA-B and HLA-C.

In one embodiment, the at least one HLA class I locus comprises HLA-A, HLA-B, and HLA-C.

In one embodiment, the at least one HLA class I locus is HLA-A.

In one embodiment, the at least one HLA class I locus is HLA-B.

In one embodiment, the at least one HLA class I locus is HLA-C.

In one embodiment, the at least one HLA class I locus is HLA-A and HLA-B.

In one embodiment, the at least one HLA class I locus is HLA-A and HLA-C.

In one embodiment, the at least one HLA class I locus is HLA-B and HLA-C.

In one embodiment, the at least one HLA class I locus is HLA-A, HLA-B, and HLA-C.

In one embodiment, the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class II locus comprises HLA-DRB1.

In one embodiment, the at least one HLA class II locus comprises HLA-DRB3.

In one embodiment, the at least one HLA class II locus comprises HLA-DRB4.

In one embodiment, the at least one HLA class II locus comprises HLA-DRB5.

In one embodiment, the at least one HLA class II locus comprises HLA-DQA1.

In one embodiment, the at least one HLA class II locus comprises HLA-DPA1.

In one embodiment, the at least one HLA class II locus comprises HLA-DQB1.

In one embodiment, the at least one HLA class II locus comprises HLA-DPB1.

In one embodiment, the at least one HLA class II locus is HLA-DRB1.

In one embodiment, the at least one HLA class II locus is HLA-DRB3.

In one embodiment, the at least one HLA class II locus is HLA-DRB4.

In one embodiment, the at least one HLA class II locus is HLA-DRB5.

In one embodiment, the at least one HLA class II locus is HLA-DQA1.

In one embodiment, the at least one HLA class II locus is HLA-DPA1.

In one embodiment, the at least one HLA class II locus is HLA-DQB1.

In one embodiment, the at least one HLA class II locus is HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DQB1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus is selected from the group consisting of HLA-DRB1, HLA-DQB1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus comprises HLA-DRB1, HLA-DQB1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus comprises HLA-DRB1, HLA-DQB1, and HLA-DPB1.

In one embodiment, the at least one HLA class I locus comprises HLA-A and HLA-B, and the at least one HLA class II locus comprises HLA-DRB1.

In one embodiment, the at least one HLA class I locus comprises HLA-A and HLA-B, and the at least one HLA class II locus is HLA-DRB1.

Software of the Invention

Certain features and embodiments of the invention comprise software and the use of software. For example, DNA sequencing typically uses specific software that converts data collected from Sanger sequencing performed by a DNA sequencing device into a DNA sequence. Both DNA sequencing devices and DNA sequencing software are commercially available from, for example, Applied Biosystems, Inc., and such commercially available DNA sequencing devices and related DNA sequencing software can be used in conjunction with the methods and other aspects of the invention.

Similarly, sequence-specific oligonucleotide probe hybridization typically uses specific software that converts data collected from a probe hybridization or flow analyzer device into the presence or absence of a DNA sequence (represented by each probe). For example, HLA Fusion™ software (One Lambda, Canoga Park, Calif.) interprets the pattern of probe hybridization or lack of hybridization by comparing probe sequences to a database of reference HLA sequences, for example, the HLA allele and sequence database found at ebi.ac.uk/ipd/imgt/hla. HLA Fusion™ software provides a list of HLA genotypes compatible with the hybridization results, and it provides a report with the hybridization profile and the HLA assignment. Both probe hybridization or flow analyzer devices and related software are commercially available from, for example, LABScan™ flow analyzer (Luminex Corp., Austin, Tex.), and such commercially available devices and related software can be used in conjunction with the methods and other aspects of the invention.

Assign ATF software, described herein, is part of the present invention. This software assembles individual DNA sequences into a contiguous sequence and makes HLA assignments based on the assembled DNA sequence. Assign ATF makes assignments by comparing assembled sequence information to a database of reference HLA sequences (for example, the HLA allele and sequence database found at ebi.ac.uk/ipd/imgt/hla). Assign ATF provides a list of HLA genotypes compatible with the sequence, and it provides a report with the sequence(s) and the HLA assignment(s).

In one embodiment, Assign ATF software comprises a computer program product residing on a non-transitory computer-readable medium having a plurality of instructions stored thereon which, when executed by a computer processor, cause that computer processor to:

(a) assemble, from one or more input nucleotide sequences for any one HLA class I locus or HLA class II locus, a single contiguous nucleotide sequence for each allele of said locus, thereby generating one or two single contiguous nucleotide sequences for said locus;

(b) compare the one or two assembled single contiguous nucleotide sequences to a database associating nucleotide sequences with corresponding HLA alleles; and (c) output a list of HLA genotypes compatible with the one or two assembled single contiguous nucleotide sequences for said locus.

Allelos software, described herein, is part of the present invention. This laboratory management and interface software tracks samples and data through the typing process. It also compares HLA assignments based on DNA sequencing with HLA assignments based on probe-based (SSOP) hybridization and identifies discrepancies. For example, Allelos compares HLA assignments made by Assign ATF with HLA assignments made by HLA Fusion™ software. In addition to identifying discrepancies, Allelos compares the assignments from the sequencing pathway and assignments from the hybridization pathway and (i) identifies those genotypes that are present in both and (ii) excludes those genotypes that are present in only one pathway. This produces a result that has higher resolution than the assignment achieved by either pathway (i.e., SBT or hybridization) alone. For example, if SBT gives 1+2 or 3+4 and hybridization gives 1+2 or 5+6 or 7+8, the program gives the overlapping genotype 1+2 as the final assignment. The 1+2 is the G-level assignment. Allelos also generates a report of HLA assignments in various formats.

In one embodiment, Allelos software comprises a computer program product residing on a non-transitory computer-readable medium having a plurality of instructions stored thereon which, when executed by a computer processor, cause that computer processor to:

(a) compare (i) input HLA assignments based on nucleotide sequence information for the at least one HLA class I locus, the at least one HLA class II locus, or both the at least one HLA class I locus and the at least one HLA class II locus and (ii) input HLA assignments based on hybridization data for the at least one HLA class I locus, the at least one HLA class II locus, or both the at least one HLA class I locus and the at least one HLA class II locus;

(b) identify any discrepancies between the input HLA assignments based on nucleotide sequence information and the input HLA assignments based on hybridization data; and (c) identify those genotypes that are present in both the input HLA assignments based on nucleotide sequence information and the input HLA assignments based on hybridization data, and exclude those genotypes that are present in only one of the input HLA assignments based on nucleotide sequence information and the input HLA assignments based on hybridization data.

This produces a result that has a higher resolution than the assignment achieved by either SBT or hybridization alone.

Kits of the Invention

An aspect of the invention is a kit comprising a first set of oligonucleotide primers for polymerase chain reaction (PCR) amplification of at least one human leukocyte antigen (HLA) class I locus, at least one HLA class II locus, or both at least one HLA class I locus and at least one HLA class II locus of a subject; and a second set of oligonucleotide primers for performing one-step DNA sequencing of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject.

In one embodiment, the first set of oligonucleotide primers comprises oligonucleotide primers having nucleotide sequences selected from the group consisting of SEQ ID NOs 1-29.

In one embodiment, the second set of oligonucleotide primers comprises oligonucleotide primers having nucleotide sequences selected from the group consisting of SEQ ID NOs 4 and 30-54.

In one embodiment, the first set of oligonucleotide primers comprises oligonucleotide primers having nucleotide sequences selected from the group consisting of SEQ ID NOs 1-29, and the second set of oligonucleotide primers comprises oligonucleotide primers having nucleotide sequences selected from the group consisting of SEQ ID NOs 4 and 30-54.

In one embodiment, the at least one HLA class I locus is selected from the group consisting of HLA-A, HLA-B, and HLA-C.

In one embodiment, the at least one HLA class I locus comprises HLA-A.

In one embodiment, the at least one HLA class I locus comprises HLA-B.

In one embodiment, the at least one HLA class I locus comprises HLA-C.

In one embodiment, the at least one HLA class I locus comprises HLA-A and HLA-B.

In one embodiment, the at least one HLA class I locus comprises HLA-A and HLA-C.

In one embodiment, the at least one HLA class I locus comprises HLA-B and HLA-C.

In one embodiment, the at least one HLA class I locus comprises HLA-A, HLA-B, and HLA-C.

In one embodiment, the at least one HLA class I locus is HLA-A.

In one embodiment, the at least one HLA class I locus is HLA-B.

In one embodiment, the at least one HLA class I locus is HLA-C.

In one embodiment, the at least one HLA class I locus is HLA-A and HLA-B.

In one embodiment, the at least one HLA class I locus is HLA-A and HLA-C.

In one embodiment, the at least one HLA class I locus is HLA-B and HLA-C.

In one embodiment, the at least one HLA class I locus is HLA-A, HLA-B, and HLA-C.

In one embodiment, the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class II locus comprises HLA-DRB1.

In one embodiment, the at least one HLA class II locus comprises HLA-DRB3.

In one embodiment, the at least one HLA class II locus comprises HLA-DRB4.

In one embodiment, the at least one HLA class II locus comprises HLA-DRB5.

In one embodiment, the at least one HLA class II locus comprises HLA-DQA1.

In one embodiment, the at least one HLA class II locus comprises HLA-DPA1.

In one embodiment, the at least one HLA class II locus comprises HLA-DQB1.

In one embodiment, the at least one HLA class II locus comprises HLA-DPB1.

In one embodiment, the at least one HLA class II locus is HLA-DRB1.

In one embodiment, the at least one HLA class II locus is HLA-DRB3.

In one embodiment, the at least one HLA class II locus is HLA-DRB4.

In one embodiment, the at least one HLA class II locus is HLA-DRB5.

In one embodiment, the at least one HLA class II locus is HLA-DQA1.

In one embodiment, the at least one HLA class II locus is HLA-DPA1.

In one embodiment, the at least one HLA class II locus is HLA-DQB1.

In one embodiment, the at least one HLA class II locus is HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DQB1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus is selected from the group consisting of HLA-DRB1, HLA-DQB1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus comprises HLA-DRB1, HLA-DQB1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus comprises HLA-DRB1, HLA-DQB1, and HLA-DPB1.

In one embodiment, the at least one HLA class I locus comprises HLA-A and HLA-B, and the at least one HLA class II locus comprises HLA-DRB1.

In one embodiment, the at least one HLA class I locus comprises HLA-A and HLA-B, and the at least one HLA class II locus is HLA-DRB1.

Systems of the Invention

An aspect of the invention is a system comprising a first set of oligonucleotide primers for polymerase chain reaction (PCR) amplification of at least one human leukocyte antigen (HLA) class I locus, at least one HLA class II locus, or both at least one HLA class I locus and at least one HLA class II locus of a subject; a second set of oligonucleotide primers for performing one-step DNA sequencing of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject; and a set of oligonucleotide probes for performing sequence-specific probe hybridization of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject.

In one embodiment, the system further comprises a computer program product residing on a non-transitory computer-readable medium having a plurality of instructions stored thereon which, when executed by a computer processor, cause that computer processor to:

(a) assemble, from one or more input nucleotide sequences for any one HLA class I locus or HLA class II locus, a single contiguous nucleotide sequence for each allele of said locus, thereby generating one or two single contiguous nucleotide sequences for said locus;

(b) compare the one or two assembled single contiguous nucleotide sequences to a database associating nucleotide sequences with corresponding HLA alleles; and (c) output a list of HLA genotypes compatible with the one or two assembled single contiguous nucleotide sequences for said locus.

In one embodiment, the system further comprises a computer program product residing on a non-transitory computer-readable medium having a plurality of instructions stored thereon which, when executed by a computer processor, cause that computer processor to:

(a) compare (i) input HLA assignments based on nucleotide sequence information for the at least one HLA class I locus, the at least one HLA class II locus, or both the at least one HLA class I locus and the at least one HLA class II locus and (ii) input HLA assignments based on hybridization data for the at least one HLA class I locus, the at least one HLA class II locus, or both the at least one HLA class I locus and the at least one HLA class II locus; and (b) identify any discrepancies between the input HLA assignments based on nucleotide sequence information and the input HLA assignments based on hybridization data; and (c) identify those genotypes that are present in both the input HLA assignments based on nucleotide sequence information and the input HLA assignments based on hybridization data, and exclude those genotypes that are present in only one of the input HLA assignments based on nucleotide sequence information and the input HLA assignments based on hybridization data.

This produces a result that has a higher resolution than the assignment achieved by either SBT or hybridization alone.

In one embodiment, the system further comprises both of the computer program products just described.

In one embodiment, the first set of oligonucleotide primers comprises oligonucleotide primers having nucleotide sequences selected from the group consisting of SEQ ID NOs 1-29.

In one embodiment, the second set of oligonucleotide primers comprises oligonucleotide primers having nucleotide sequences selected from the group consisting of SEQ ID NOs 4 and 30-54.

In one embodiment, the first set of oligonucleotide primers comprises oligonucleotide primers having nucleotide sequences selected from the group consisting of SEQ ID NOs 1-29, and the second set of oligonucleotide primers comprises oligonucleotide primers having nucleotide sequences selected from the group consisting of SEQ ID NOs 4 and 30-54.

In one embodiment, the at least one HLA class I locus is selected from the group consisting of HLA-A, HLA-B, and HLA-C.

In one embodiment, the at least one HLA class I locus comprises HLA-A.

In one embodiment, the at least one HLA class I locus comprises HLA-B.

In one embodiment, the at least one HLA class I locus comprises HLA-C.

In one embodiment, the at least one HLA class I locus comprises HLA-A and HLA-B.

In one embodiment, the at least one HLA class I locus comprises HLA-A and HLA-C.

In one embodiment, the at least one HLA class I locus comprises HLA-B and HLA-C.

In one embodiment, the at least one HLA class I locus comprises HLA-A, HLA-B, and HLA-C.

In one embodiment, the at least one HLA class I locus is HLA-A.

In one embodiment, the at least one HLA class I locus is HLA-B.

In one embodiment, the at least one HLA class I locus is HLA-C.

In one embodiment, the at least one HLA class I locus is HLA-A and HLA-B.

In one embodiment, the at least one HLA class I locus is HLA-A and HLA-C.

In one embodiment, the at least one HLA class I locus is HLA-B and HLA-C.

In one embodiment, the at least one HLA class I locus is HLA-A, HLA-B, and HLA-C.

In one embodiment, the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class II locus comprises HLA-DRB1.

In one embodiment, the at least one HLA class II locus comprises HLA-DRB3.

In one embodiment, the at least one HLA class II locus comprises HLA-DRB4.

In one embodiment, the at least one HLA class II locus comprises HLA-DRB5.

In one embodiment, the at least one HLA class II locus comprises HLA-DQA1.

In one embodiment, the at least one HLA class II locus comprises HLA-DPA1.

In one embodiment, the at least one HLA class II locus comprises HLA-DQB1.

In one embodiment, the at least one HLA class II locus comprises HLA-DPB1.

In one embodiment, the at least one HLA class II locus is HLA-DRB1.

In one embodiment, the at least one HLA class II locus is HLA-DRB3.

In one embodiment, the at least one HLA class II locus is HLA-DRB4.

In one embodiment, the at least one HLA class II locus is HLA-DRB5.

In one embodiment, the at least one HLA class II locus is HLA-DQA1.

In one embodiment, the at least one HLA class II locus is HLA-DPA1.

In one embodiment, the at least one HLA class II locus is HLA-DQB1.

In one embodiment, the at least one HLA class II locus is HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus is selected from the group consisting of HLA-DRB1, HLA-DQB1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus is selected from the group consisting of HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus is selected from the group consisting of HLA-DRB1, HLA-DQB1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus is selected from the group consisting of HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus is selected from the group consisting of HLA-A, HLA-B, and HLA-C, and the at least one HLA class II locus comprises HLA-DRB1, HLA-DQB1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DRB3, HLA-DRB4, HLA-DRB5, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRA, HLA-DRB1, HLA-DQA1, HLA-DQB1, HLA-DPA1, and HLA-DPB1.

In one embodiment, the at least one HLA class I locus comprises HLA-A, HLA-B, and HLA-C, and the at least one HLA class II locus comprises HLA-DRB1, HLA-DRB3, HLA-DRB4, HLA-DRB5, HLA-DQB1, and HLA-DPB1.

In one embodiment, the at least one HLA class I locus comprises HLA-A, HLA-B, and HLA-C, and the at least one HLA class II locus comprises HLA-DRB1, HLA-DQB1, and HLA-DPB1.

In one embodiment, the at least one HLA class I locus comprises HLA-A and HLA-B, and the at least one HLA class II locus comprises HLA-DRB1.

In one embodiment, the at least one HLA class I locus comprises HLA-A and HLA-B, and the at least one HLA class II locus is HLA-DRB1.

EXAMPLES

The invention now being generally described, it will be more readily understood by reference to the following examples which are included merely for purposes of illustration of certain aspects and embodiments of the present invention, and are not intended to limit the invention.

Example 1

DNA Extraction Using QIAamp® DNA Blood Kit Spin Columns

This example, which has been reduced to practice, describes the QIAamp spin column procedure for extracting DNA from any of a variety of samples, e.g., whole blood, peripheral blood lymphocytes (PBL), and buccal swabs.

Principle:

DNA is released from the cell nucleus as it is lysed and digested in lysis buffer with QIAGEN Protease, which is completely free of DNAase and RNAase activity. A proteinase enzyme degrades proteins bound to the DNA. DNA is adsorbed onto the QIAamp silicon membrane affinity column. After two washes to remove residual contaminants, purified DNA is eluted from membrane in AE buffer or water. The QIAamp procedure is optimized for volumes of 200 μL, but this sometimes fails to yield sufficient DNA. The protocol may be modified (as recommended by Qiagen) by increasing the volume of sample used in order to increase total DNA yield.

Specimen:

Whole blood, cord blood, related samples (e.g., red cell pellets), cell pellets, buccal swabs, or peripheral blood lymphocytes (PBL).

Reagents and Equipment:

QIAamp DNA Blood Mini Kit
96-100% ethanol
Reagent grade water
1×PBS (Phosphate Buffered Saline) pH 7.2 (Gibco)
Protease (20 mg/mL)
Proteinase K (20 mg/mL)
Heat block or water bath
Vortex mixer
Microcentrifuge Reagent Preparation:

Buffer AL is provided by QIAGEN ready for use.

Buffers AW1 and AW2 are provided by QIAGEN as concentrates. Working buffers are prepared from the concentrates by dilution with an appropriate amount of 96-100% ethanol according to supplier's instructions.

QIAGEN Protease is provided by QIAGEN as a powder. A working solution of protease is prepared by adding the supplied solvent and mixing.

Procedure:

DNA Extraction from Whole Blood, PBL, Cell Pellet, and Buccal Swab Samples:

1. Turn on heat block or water bath to 56° C. and allow to reach temperature.

Label the appropriate number of 1.5 mL microfuge tubes and QIAGEN spin columns with sample ID.

2. Add 200 μL sample or swab (place the swab in the tube and snap off the end of the applicator) to the tube. If the sample volume is less than 200 μL, add PBS to bring sample to volume. For buccal swab samples, add 400 μL PBS.
3. Pipet 20 μL QIAGEN Protease into the microcentrifuge tube.
4. Add 200 μL Buffer AL to the sample (for buccal swabs, add 400 μL Buffer AL). Mix by vortex for 15 sec.
5. Incubate at 56° C. for 10 minutes.
6. Briefly centrifuge the microcentrifuge tube to remove condensation drops from the inside of the lid.
7. Add 200 μL 96-100% ethanol to the sample (for buccal swabs add 400 μL) and mix again by vortex for 15 seconds. Again briefly centrifuge the microcentrifuge tube.
8. Carefully apply the lysate to the QIAamp spin column in a collection tube without wetting the rim. Centrifuge at 6000×g (8000 rpm) for 1 min Place the QIAamp spin column into a clean 2-mL collection tube and discard the tube containing the filtrate. Perform this step twice for buccal swab samples as the volume of the lysate is too much for once.
9. After placing the spin column into a clean collection tube, carefully add 500 μL Buffer AW1 without wetting the rim. Centrifuge at 6000×g (8000 rpm) for 1 min. Place the spin column into a clean 2-mL collection tube and discard tube with the filtrate.
10. Carefully add 500 μL Buffer AW2 without wetting the rim. Centrifuge at 20,000×g (14,000 rpm) for 3 minutes to ensure there is no residual Buffer AW2 as it may cause problems in downstream applications.
11. Place the QIAamp spin column in a clean 1.5 mL microcentrifuge tube and discard the tube with the filtrate. Add 200 μL $H_2O$ and incubate at room temperature for 1-5 minutes (if re-extracting a problem buccal swab, add 100 μL). Centrifuge at 6000×g (8000 rpm) for 1 min.
12. Discard the spin column. Store at 4° C. for short term, or −20° C. to −80° C. for long term storage.

Example 2

DNA Extraction Using QIAamp® 96 Spin Blood Kit

This example, which has been reduced to practice, describes a method to extract genomic DNA from cryopreserved blood, fresh whole blood, red cell pellets, or buccal swabs.

Principle:

Blood, red cell pellets, or buccal cells are lysed and digested in lysis buffer with QIAGEN Protease, which is completely free of DNAase and RNAase activity. DNA is adsorbed onto the QIAamp silicon membrane. After two washes to remove residual contaminants, purified DNA is eluted in water. Usually, 200 μL of blood or one buccal swab can yield 4-10 μg of pure DNA. Extracted DNA can be stored at 4° C. for at least one year and at −20° C. to −80° C. for a longer period of time.

Specimen:

Whole blood, buccal swabs, or red cell pellets

Reagents and Equipment:

QIAamp 96 Blood Spin Kit
Sigma 6-10 Centrifuge with rotor #09100
70° C. Incubator
Multichannel pipettor with tips
Ethyl Alcohol (96%-100%)
1×PBS (Phosphate Buffered Saline) pH 7.2 (Gibco)
Vortex mixer
Shaker
Reagent grade water Reagent Preparation:

1. QIAGEN Protease Stock Solution:

Add one vial of protease solvent to each bottle containing lyophilized QIAGEN Protease provided in the kit.

2. Buffer AL:

Buffer AL is provided by QIAGEN ready for use.

3. Buffer AW1:

Add 230 mL of 96-100% ethanol to Buffer AW1 concentrate when using large bottles.

4. Buffer AW2:

Add 640 mL of 96-100% ethanol to Buffer AW2 concentrate when using large bottles.

Procedure:

A. DNA Extraction from Whole Blood and Red Cell Pellet Samples:
- A1. Remove two or four pre-aliquoted round-well blocks of whole blood from freezer. If the sample volume is less than 200 µL, add PBS to bring sample to 200 µL volume.
- A2. Pipet 30 µL of QIAGEN protease into each well of the round-well blocks. Vortex trays gently to mix.
- A3. Add 200 µL of Buffer AL to each sample. Seal the wells with the caps provided.
- A4. Mix thoroughly by shaking for at least 15 seconds. Spin for one minute at 3000 rpm to remove any solution from caps.
- A5. Incubate blocks at 70° C. for at least 10 minutes in an incubator. Remove from incubator and spin for one minute at 3000 rpm to remove any solution from caps as needed.
- A6. Remove the caps and add 210 µL of ethanol to each well. Seal with new caps and mix thoroughly for at least 15 seconds. Spin for one minute at 3000 rpm.
- A7. Place a QIAamp plate on top of an S-block and mark plate with tray number.
- A8. Apply mixture from round well block to corresponding QIAamp plate. (~635 µL/well)
- A9. Seal QIAamp plate with air pore tape provided in kit. Centrifuge at 6000 rpm for 4 minutes.
- A10. Remove tape and add 500 µL of Buffer AW1 to each well. Seal with new tape, and spin at 6000 rpm for 2 minutes.
- A11. Remove tape and add 500 µL of Buffer AW2 to each well. Seal with new tape, and spin at 6000 rpm for 4 minutes.
- A12. Remove tape and incubate QIAamp plates for at least 15 minutes in a 70° C. incubator. Place plates on side to facilitate drying of membrane.
- A13. Label collection microtube racks with appropriate tray ID. Make sure centrifuge adaptor is in place prior to placing QIAmp plate on rack. Place QIAamp plate on top of a collection microtube rack.
- A14. Add 200 µL of preheated water to each well. Seal with new tape. Incubate for one minute at room temperature. Centrifuge at 6000 rpm for 4 minutes.
- A15. Repeat step A14.

B. DNA Extraction from Buccal Swab Samples:
- B1. Remove two or four pre-aliquoted square-well blocks of buccal swabs and appropriate tray identifiers from freezer.
- B2. Add 100 µL of each tray identifier to the appropriate well.
- B3. Add 400 µL of 1×PBS into each well of the square-well blocks.
- B4. Pipet 30 µL of QIAGEN protease into each well of the square-well blocks.
- B5. Add 400 µL of Buffer AL to each sample. Seal the wells with a tray seal.
- B6. Mix thoroughly with vortex. Place blocks on shaker for 5 minutes with speed set to 6.
- B7. Incubate blocks at 70° C. for at least 10 minutes in an incubator. Vortex blocks after the first 10 minute incubation.
- B8. Remove tray seals and add 400 µL of ethanol to each well. Seal the wells with a tray seal and mix gently with vortex. Place blocks on shaker until ready for transfer to QIAamp plate with speed set to 3.
- B9. Place a QIAamp plate on top of a waste S-block and mark plate with tray number.
- B10. Apply mixture from round well block to corresponding QIAamp plate (~1050 µL/well). Pipet mixture up and down once to facilitate mixing before dispensing into QIAamp plate.
- B11. Seal QIAamp plate with air pore tape provided in kit. Centrifuge at 6000 rpm for 4 minutes.
- B12. Remove tape and add 500 µL of Buffer AW1 to each well. Seal with new tape, and spin at 6000 rpm for 2 minutes.
- B13. Remove tape and add 500 µL of Buffer AW2 to each well. Seal with new tape, and spin at 6000 rpm for 4 minutes.
- B14. Remove tape and incubate QIAamp plates for at least 15 minutes in a 70° C. incubator. Place plates on side to facilitate drying of membrane.
- B15. Label collection microtube racks with appropriate tray ID. Make sure centrifuge adaptor is in place prior to placing QIAmp plate on rack. Place QIAamp plate on top of a collection microtube rack.
- B16. Add 80 µl, or 100 µL (for sequence-based typing), or 200 µL (for SSOP typing) of preheated water to each well. Seal with new tape. Incubate for one minute at room temperature. Centrifuge at 6000 rpm for 4 minutes.

Example 3

DNA Isolation and Purification Using Robotic Workstation

This example, which has been reduced to practice, describes Qiagen automated technology for isolation and purification of genomic DNA from various blood and tissue products based on the use of magnetic particles. The isolation relies upon the binding of DNA to the silica surface of the magnetic beads in the presence of a chaotropic salt solution. The magnetic particles with DNA attached are separated from the lysates using a magnet. The DNA is then washed and eluted with a buffer. The eluate containing the DNA is transferred to a clean tube as a final product for HLA typing. A batch run typically includes 6 samples. There are two EZ1 Pre-programmed Memory Cards: one for whole blood/PBL and one for buccal swabs.

Specimen

Whole blood, peripheral blood lymphocytes (PBL), or buccal swabs

Materials and Reagents

EZ1 Biorobot/EZ1 Advanced XL

EZ1 Card/EZ1 Advanced Card for protocol required (whole blood or swab)

EZ1 DNA blood kit or EZ1 DNA tissue kit containing reagent cartridge

Disposable tip holders

Disposable filter tips 2 mL sample tubes 1.5 mL elution tubes

Buffer G2

Proteinase K

Procedure

1. Instrument

The EZ1 Biorobot instrument has 6 positions; there are 6 positions available for loading samples on the worktable. The EZ1 Advanced XL instrument has 14 positions; there are 14 positions available for loading samples on the worktable.

2. Tube labeling
   2.1 Label 2 mL sample tubes with sample ID numbers.
   2.2 Label 1.5 mL elution tubes with the same sample ID numbers.
3. For Whole Blood/PBL protocol: Transfer 200 µL whole blood/PBL to the properly labeled sample tubes.
4. For Buccal Swab protocol: Cut or break off the end part of the swab into a 2 mL sample tube.
   4.1 Add 200 µL of Millipore water. Add 190 µL of Buffer G2 to the sample. Ensure that the tip of the swab is fully submerged.
   4.2 Add 10 µL of Proteinase K solution and mix thoroughly by vortex for 10 seconds.
   4.3 Incubate at 56° C. for 15 minutes. Vortex the tube 1-2 times during the incubation.
   4.4 Centrifuge the tube briefly to remove condensation.
   4.5 Remove and discard the swab from the tube. Using sterile forceps, press the swab against the inside of the tube to obtain maximum sample volume. The sample volume should be approximately 200 µL.
5. Use the correct EZ1 card/EZ1 Advanced card for the protocol (blood vs swab).
6. Instrument worktable set-up
   6.1 Remove the sample/tip rack and the cartridge rack from the worktable.
   6.2 Take out the reaction cartridges; invert those several times to mix. Place them on the rack.
   6.3 Tap the Reaction Cartridges gently to force reagent to the bottom of the wells, without creating bubbles.
   6.4 Slide in the Reaction Cartridges to the direction of the arrow pointing until the resistance is felt, then press downward with your thumb until the "click" noise is heard.
   6.5 Place the cartridge rack on the worktable. Be sure that the two heating positions of each cartridge fit into the heating system.
   6.6 Place the sample/tip rack on the worktable. Elution tubes are loaded into the first row. Tip holders containing filter-tips are loaded into second row. Third row is empty. Sample tubes are loaded into the fourth row.
   6.10 Close the workstation door.
7. Start the isolation protocol by pressing the START key.
8. At the end of a batch run, retrieve the labeled elution tubes containing the final product and cap them carefully. The DNA is ready to use, or can be stored at 2-8° C. for a short period or at −20° C. for longer periods.

Example 4

Amplification of DNA Using Polymerase Chain Reaction (LABType® Protocol)

This example, which has been reduced to practice, describes how to specifically amplify DNA encoding HLA class I-A, -B, and -C alleles, HLA class I group-specific alleles, and HLA class II-DR, -DQ, and -DP alleles.

Principle:
   Double-stranded genomic DNA is denatured at 96° C. HLA class I and class II locus/group-specific oligonucleotide primers, which are biotin-labeled, for exons 2 and 3 (HLA-A, -B, -C) and for exon 2 (HLA-DRB1, -DQB1, -DPB1, -DQA1, -DPA1) anneal to the denatured DNA template strands at 60° C. Taq polymerase adds available nucleotides (dNTPs) onto the primers in a 72° C. extension reaction, thereby producing complementary copies of the single-stranded DNA. Repetition of the cycles of denaturation, annealing, and extension generates billions of copies of the selected DNA sequence defined by the primers.

Specimen:
   Extracted DNA

Reagents and Equipment:
   Locus- or Group-Specific Primer Set
   DMix (Reaction buffer provided with Taq polymerase)
   Taq Polymerase (Roche Applied Science #3734935001)
   Thermal Cycler (Applied Biosytems 2700 or 2720)
   Multi-channel pipette & tips
   Pipettes & tips
   Vortex mixer
   Microcentrifuge
   PCR tray bases
   Semi-skirted PCR trays (CLP/VWR—3442.X or Denville C18082-10)
   8 mL sterile disposable tubes
   Tape seals
   Reagent reservoirs
   Ice packs Procedure:
   A. Thermal Cycler Preparation:
      Turn on the appropriate number of thermal cyclers and start the 'hold 60' program.
   B. Pre-PCR Area Clean-up:
      Thoroughly clean lab surfaces with 10% bleach and/or 70% ethanol to remove contamination with amplified DNA.
   C. PCR Tray Assembly:
      Use tray bases that have been previously rinsed in 10% bleach and returned to pre-PCR room. Place semi-skirted PCR tray on PCR tray base and label trays with locus, panel, and tech initials.
   D. Transfer of DNA Sample:
      1. For custom trays (e.g., FV trays):
      Aliquot DNA sample into each well using sterile filter pipette tips.
      No-DNA control(s) (PCR reactions lacking DNA) can be used to check for cross-contamination.
      2. For 96-well trays of DNA prepared by QIAgen:
      i. Verify correct panel name and correct tray orientation when transferring DNA to the PCR tray. Aliquot DNA samples into each well using sterile filter pipette tips and a 12-channel pipettor or with the Bravo™. Manually add a QC sample to well D11.
      96-well QIAgen trays already contain the No-DNA control in well locations D12 and H12.
      ii. Reseal 96-well QIAgen DNA tray with new tape seal and store appropriately.
   E. Preparation of PCR Master Mix:
      1. Thaw the appropriate amount of DMix and Primer Mix and keep on ice. Vortex 15 seconds before using and either shake down contents or centrifuge for 3-5 seconds.
      2. In an 8 mL sterile disposable tube, assemble the PCR master mix according to the recipe below. Briefly centrifuge the Taq polymerase before adding to the PCR master mix. Keep mix on ice pack.
      3. Invert the Master Mix several times to evenly distribute the reagents and vortex 15 seconds. Pour the completed PCR master mix into a clean reagent reservoir placed on ice pack.
      4. Immediately add the appropriate amount of PCR master mix to each of the PCR reaction tubes using a multichannel or individual pipette. Use fresh tips for each row.
      5. Place tape seal over entire tray.

F. Exemplary PCR Master Mix (volumes per DNA sample):

| | |
|---|---|
| DMix | 6.9 μL |
| Primer Mix | 2.0 μL |
| Taq | 0.1 μL |
| Total volume | 9.0 μL |

For each individual PCR reaction, 9.0 μL of PCT Master Mix is added to 2.0 μL of DNA sample.

G. Transfer to Thermocycler:
1. Inspect each sample well for air bubbles by looking upward through the bottom of the tray. Remove any air by flicking the well with finger. Keep tray(s) on ice pack.
2. Remove lab coat and leave the pre-PCR room. Stop the 'hold 60' program and start the 'luminex per' program. For FTA disks (HLA-A or -B only) use the 'fta per' program. Place the PCR tray into the thermal cycler after the temperature has reached 60° C.
3. After completion of cycles, store in −20° C. to −80° C. freezer until hybridization.

Example 5

Class I Amplification and Sequencing (HLA-A, -B, and -C Loci)

This example, which has been reduced to practice, describes how polymerase chain reaction (PCR) using sequence-specific primers and Taq polymerase is used to both amplify and sequence DNA samples for class I HLA typing (HLA-A, -B, and -C loci).

Principle:
Amplification of class I HLA-A, -B and -C loci is carried out using locus-specific genomic PCR as described by K. Cao et al., Rev Immunogenetics 1:177-208 (1999). Unincorporated primers and nucleotides are removed from the amplified DNA using AMPure. This kit adds magnetic beads that bind DNA. Once purified, the amplified DNA is sequenced using BigDye® Terminator (BDT) chemistry (Applied Biosystems, Foster City, Calif.). If results are several alternative allele combinations, additional sequencing primers are used to define alleles.

Specimen:
Genomic DNA extracted with Qiagen Kit.

Reagents and Equipment:
PCR:
ABC buffer
DMSO (cat #D-2650, Sigma)
PCR primers (See Example 14)
dNTPs (10 mM) (cat #11581295001, Roche)
Taq polymerase (5 U/μL) (cat #1435094, Roche)
Pure Reagent water (cat #W4502, Sigma)
Thermal cycler
96-well semiskirted plate (cat #4332241, ISC Bioexpress)
ABC Buffer: Autoclave: for 500 mL

| | |
|---|---|
| 1M ammonium sulfate | 75 mL |
| 1M Tris (pH 8.8) | 250 mL |
| 0.5M EDTA | 0.5 mL |
| 1M MgCl$_2$ | 7.5 mL |
| 1% gelatin | 50 mL |
| Milli Q Water | qs to 500 mL |
| After autoclaving, add 14.4M beta-mercaptoethanol | 3450 μL |

Mix, aliquot 1.5 mL, label appropriately and store at 4° C. Biomek multichannel automation station (Cat #A31841, Beckman Coulter) Bravo multichannel automation station (Cat #16050, Velocity 11)

PCR Purification:
AMPure (CAT #00130, Agencourt Bio-Science Corp.)
200 Proof EtOH (cat #6505001050000, Warner-Graham Company)
70% EtOH
SPRI 96 magnetic plate (cat #00219, Agencourt Bio-Science Corp.)

Sequencing Reaction:
96-well plate
BigDye® Terminator V1.1 cycle sequencing kit (cat #4337452, ABI)
Sequencing primers 0.8 μM (See Example 15)
Thermal cycler
Centrifuge Procedure:
A. Use genomic DNA purified using Qiagen methodology as described in Example 1, 2, or 3.
B. PCR Master Mix
  1. For small volume of samples:

| Class I PCR Mix (1X) | |
|---|---|
| Reagent Water | 32.75 μL |
| ABC Buffer | 5 μL |
| DMSO | 5 μL |
| FP—forward primer (20 μM)** | 0.5 μL |
| RP—reverse primer (20 μM)** | 0.5 μL |
| dNTP (10 mM) | 1 μL |

**The HLA-B PCR primer pair for locus-specific amplification is a mixture of 3 primers to insure that all HLA-B alleles are amplified. Mix the diluted primers in the following ratio: 0.5 μL 20 μM Bex1-BT; 0.25 μL 20 μM 3B1-AC; 0.5 μL 20 μM 3B1

Make enough Master Mix for 500 samples, mix well. Select 3 reference samples to QC the PCR Master Mix. Document the results.

Aliquot 1.5 mL into 1.5 mL tube, label appropriately and store at −20° C. for future use.

2. For large volume of samples:

| Class I PCR Mix (1X) | |
|---|---|
| Reagent Water | 16.4 μL |
| ABC Buffer | 2.5 μL |
| DMSO | 2.5 μL |
| FP—forward primer (20 μM)** | 0.25 μL |
| RP—reverse primer (20 μM)** | 0.25 μL |
| dNTP (10 mM) | 0.5 μL |

**The HLA-B PCR primer pair for locus-specific amplification is a mixture of 3 primers to insure that all HLA-B alleles are amplified. Mix the diluted primers in the following ratio: 0.25 μL 20 μM Bex1-BT; 0.125 μL 20 μM 3B1-AC; 0.25 μL 20 μM 3B1
Make enough Master Mix for 400 samples per set, mix well.

C. PCR Reactions
  For small volume of samples:
  1. Add the appropriate volume of AmpliTaq polymerase to the PCR Master Mix according to the table below.

| Number of Reactions | PCR Master Mix | AmpliTaq polymerase |
| --- | --- | --- |
| 1 | 44.75 µL | 0.25 µL |
| 10 | 447.5 µL | 2.5 µL |
| 25 | 1118.75 µL | 6.25 µL |
| 100 | 4475 µL | 25 µL |

2. Aliquot 45 µL of Master PCR/Taq mix into the wells specified on the worksheet of 96-well plate.
3. Add 5 µL of the samples of DNA specified on the worksheet. Negative control get 5 µL of dH₂O instead of DNA. 5 µL reference DNA in positive control well.
4. Cap plate tightly with rubber plate cover, place in thermal cycler, close and tighten lid.

NOTE: A positive and negative control should be run for each PCR batch. Use a molecularly characterized DNA such as a cell line with known HLA-A, -B, -C for a positive control. This checks for PCR reaction set up and quality of test DNA. The negative control (H₂O instead of DNA) checks for contamination with previously amplified DNA.

5. PCR conditions and amplification

| A and B locus: | A and B locus for buccal swab: | C locus: |
| --- | --- | --- |
| 1. 94° C. for 2 min | 1. 94° C. for 2 min | 1. 94° C. for 2 min |
| 2. 8 cycles: | 2. 9 cycles: | 2. 39 cycles (41 for difficult samples): |
| 94° C. for 22 sec | 94° C. for 22 sec | |
| 65° C. for 50 sec | 63° C. for 50 sec | 94° C. for 22 sec |
| 72° C. for 30 sec | 72° C. for 30 sec | 59° C. for 50 sec |
| 3. 30 cycles | 3. 30 cycles | 72° C. for 30 sec |
| 94° C. for 22 sec | 94° C. for 22 sec | 3. 72° C. for 10 min |
| 62° C. for 50 sec | 60° C. for 50 sec | 4. 4° C. HOLD forever |
| 72° C.for 30 sec | 72° C. for 30 sec | |
| 4. 72° C. for 10 min | 4. 72° C. for 10 min | |
| 5. 4° C. HOLD forever | 5. 4° C. HOLD forever | |

For larger volume of samples:
1. Add the appropriate volume of AmpliTaq polymerase to the PCR Master Mix according to the table below.

| Number of Reactions | PCR Master Mix | AmpliTaq polymerase |
| --- | --- | --- |
| 1 | 22.40 µL | 0.15 µL |
| 10 | 224 µL | 1.5 µL |
| 25 | 560 µL | 3.75 µL |
| 100 | 2240 µL | 15 µL |

2. Aliquot 22.55 µL of Master PCR/Taq mix into the wells specified on the worksheet of 96-well plate.
3. Add 3 µL of the samples of DNA specified on the worksheet. Negative control get 3 µL of dH₂O instead of DNA. 3 µL reference DNA in positive control well.
4. Cap plate tightly with rubber plate cover, place in thermal cycler, close and tighten lid.
5. PCR conditions and amplification

| A locus: | AB-PCR-M: | C locus: |
| --- | --- | --- |
| 1. 94° C. for 2 min | 1. 94° C. for 2 min | 1. 94° C. for 2 min |
| 2. 35 cycles: | 2. 8 cycles: | 2. 39 cycles: |
| 94° C. for 22 sec | 94° C. for 22 sec | 94° C. for 22 sec |
| 65° C. for 50 sec | 65° C. for 50 sec | 59° C. for 50 sec |
| 72° C. for 30 sec | 72° C. for 30 sec | 72° C. for 30 sec |
| 3. 72° C. for 10 min | 3. 31 cycles | 3. 72° C. for 10 min |
| 4. 4° C. HOLD forever | 94° C. for 22 sec | 4. 4° C. HOLD forever |
| | 60° C. for 50 sec | |
| | 72° C. for 30 sec | |
| | 4. 72° C. for 10 min | |
| | 5. 4° C. HOLD forever | |

D. Template Purification of the PCR Products

Use Ampure kit to remove primers and unincorporated nucleotides following manufacturer's instructions.

For small volume of PCR product:
1. Add the PCR AMPure solution directly to the PCR reaction according to the calculation: 1.8× (reaction volume)=(volume of AMPure per reaction).
2. Mix thoroughly by pipette.
3. Place the PCR purification plate onto the SPRI plate96-R (magnetic plate) to separate the beads from the solution. Incubate approximately 5-10 minutes.
4. With PCR plate on the magnet, aspirate the cleared solution and discard.
5. Keeping the PCR plate on the magnet, dispense 200 µL 70% ethanol to each well. Allow to sit at least 30 seconds. Aspirate the wash solution, discard and repeat. Be sure to remove as much ethanol as possible to shorten the drying time.
6. Allow the PCR purification plate to air-dry completely on the bench top for about 30 minutes. Alternatively, the plate can be incubated at 37° C. no longer than 10 minutes for faster evaporation.

NOTE: Any residual alcohol will interfere with sequencing.

7. To elute DNA, add 18-40 µL (according to gel picture) of reagent water to each well, mix well. Place plate back on magnet and remove eluate containing the amplified DNA to a clean labeled plate for use.
8. The PCR reaction is now purified and ready to sequence.

For larger volume PCR products:
Use Biomek NX Multichannel Automation Workstation as described in Example 9.

E. Sequencing Reactions

Sequence using regular Class I sequencing primers (See Example 15).

NOTE: For each locus of a sample, both exon 2 and exon 3 are sequenced in the forward and reverse directions, requiring 4 primers.

1. For small volume of sequencing set up: To each tube add 2 µL diluted BigDye® Terminator (1:8), 2 µL of the appropriate primer (0.8 µM), and 2 µL of the purified PCR product.
2. For larger volume of sequencing set up: Use Bravo Multichannel Automation Workstation.
3. Cap plate tightly with rubber plate cover and quick spin the plate in the centrifuge to ensure all reagents are at the bottom of the tubes. Place rack into thermal cycler, close and tighten lid.
4. Sequencing conditions
25 cycles:
96° C. for 10 sec
50° C. for 5 sec
60° C. for 2 min
4° C. HOLD forever 5. Proceed to Example 6 for clean-up of sequencing reactions.

Example 6

Purification for Class I and Class II Sequencing Reactions

This example, which has been reduced to practice, describes methods used to remove excess dye terminators from the sequencing reaction and to prepare samples for loading onto the sequencer.

Principle:
 Removal of excess dye terminators from the sequencing reaction mixture is key in obtaining good quality sequence. Magnetic beads are used to bind DNA so that unwanted contaminants are removed in the solution. Water is used to elute DNA from the beads.

Specimen:
 Sequencing reactions from Class I Sequencing or Class II Sequencing.

Reagents and Equipment:
 Milli-Q water
 CleanSEQ purification beads solution (Agincourt APN #00121)
 SPRT plate96-R Magnet (cat #000219)
 200 Proof EtOH (Warner-Graham Company)
 73% EtOH
 Biomek NX Multichannel Automation Workstation (Cat #A31841, Beckman Coulter)

Procedure:
 For small volume of sequencing product:
 1. Add 10 µL of CleanSEQ magnetic beads solution to each well of the sequencing plate.
 2. For a 10 µL sequencing reaction, add approximately 75 µL 73% ethanol to each well and mix thoroughly.
 3. Place the sequencing plate onto the SPRIplate96-R magnet to separate the beads from solution. Incubate approximately 3 minutes.
 4. With the sequencing plate on the magnet, aspirate the cleared solution and discard.
 5. Keeping the plate on the magnet, dispense 100 µL 73% ethanol to each well and allow it to sit for at least 30 seconds. Aspirate the solution and discard.
 6. Allow the sequencing plate to air-dry completely on the bench top about 10 minutes.
 NOTE: Any residual alcohol will interfere with sequencing.
 7. Add 25-50 µL of Milli-Q water (40 mL for FTA paper) to each well, mix well by pipetting. This contains beads and DNA. The plate is now ready for loading onto the sequencer.
 8. If using ABI 3730 DNA Analyzer, keep the plate on the magnet 2-5 minutes, then transfer 15 µL to clean plate.

For larger volume of sequencing product:
Use Biomek NX Multichannel Automation Workstation as described in Example 9.

Example 7

Running the DNA Analyzer

This example, which has been reduced to practice, describes how to prepare for a run on the ABI 3730xL DNA Analyzer using purified sequencing reactions and apply the Date Collection software.

Principle:
 The ABI 3730xl DNA Analyzer is an automated, high-throughput, capillary electrophoresis system that can separate, detect and analyze up to 96 capillaries of fluorescently labeled DNA sequencing reaction in one run.

Specimen:
 BigDye®-labeled and purified DNA

Reagents and Equipment:
 ABI PRISM 3730xL DNA Analyzer (Applied Biosystems) with PC work station and color printer
 Milli-Q water
 3730 POP-7 Polymer (cat. #4332241, Applied Biosystems)
 10×3730 Running Buffer with EDTA (cat. #4335613, Applied Biosystems)
 Semi-Skirted 96-well plate (cat. #T-3085-1, ISC Bioexpress)
 Plate accessories:
 96-well plate retainer (cat.#4334869 Applied Biosystems)
 Septa seal (cat. #4315933, Applied Biosystems)
 96-well black plate base (cat. #4334873, Applied Biosystems)
 Centrifuge Procedure:
A. Prepare the sample plate
 1. Make sure that each well contains 20 µL of sequence reaction after the cleanup. Fill all empty wells with 20 µL of ddH$_2$O.
 2. Place sample plate on a level surface, lay septa flat on the plate, align the holes in the septa with plate, then press firmly to seal.
 3. Spin at 2000 RPM for 1 minute.
 4. Put sample plate in black plate base, and then snap the plate retainer onto the sample plate and base.

B. Creating the plate record:
 1. Plate records can be created in advance of placing the plates on the instrument. Data can be prepared and stored on a disk as a ".plt" file then transferred to 3730xl later.
 2. Use a default format for the plate record (3730.plt). Enter the information listed below:
  a. Container Name: SEQXXX (changes each time)
  b. Plate ID: SEQXXX (changes each time)
  c. Container type: 96-well
  d. AppTyper: Regular
  e. Plate sealing: Septa
  f. Well Name: A1-H1 order
  g. Sample name: (XXXXA_AP1)[sample ID_LOCUS_primer]
  h. Results group: SBT_RESULTS_GROUP
  i. Instrument protocol: SBT_FASTSEG50_POP7_CURRENT
  j. Analysis Protocol: SBT ANALYSIS
 3. Save on floppy diskette C. Start the Instrument:
 1. Turn the instrument on by pressing the on/off power button located on the front of the instrument. Ensure that the green instrument status light is on and constant before proceeding.
 2. Switch on the computer. Make sure that the computer is on and logged in as the proper ABI instrument. Then from the Start menu→Programs→Applied Biosystems→Data collection→Run 3730 data collection. Open the GA instruments folder located on the left side of the window. Click on ga3730 and Ting_3730 to view the instrument subfolder.

3. Import the Plate Record: Insert the floppy disk containing the saved plate record file into the computer. Click on Plate Manager (under ga3730 subfolder)→Import. Make sure that it is successfully imported into plate manager.
4. Prepare the instrument and load DNA sample plate assemblies.
   a. Make sure that the instrument's green status light is on (either flashing or constant).
   b. Make sure that adequate levels of buffer and water are in the appropriate reservoirs.
   c. Check the level of POP-7 polymer in the bottle to ensure sufficient volume for run. A minimum of 10 mL of POP-7 is required for the instrument to operate and a full run of one 96-well plate uses 250 µL of polymer.
   d. Pull out the stacker drawer. The stacker light flashes green. Open the door of the stacker tower and place up to 16 (maximum) plates into the stacker. The bottom plate will run first.
   e. Close the stacker door and the stacker drawer. The stacker light becomes a constant green.
5. To schedule a run using manual model:
   a. From the Run Scheduler tab (under Ting_3730 subfolder) of the Data collection window. Click Search→Find All→Add Plates.
   b. Add all plates in the batch of runs. Make sure all plates are added in the correct run order. Once all plates have been added, click "Done".
   c. Click on the green arrow located in the upper left corner of the Data Collection window to start the run. A dialog box will open confirming the instrument is properly set up and ready to start. Before clicking "OK", double-check to make sure instrument has sufficient fluids and the plates are stacked and imported in correct run order.

Example 8

Sequence Analysis with Windows/Assign

This example, which has been reduced to practice, describes how to obtain allelic typing through analysis of samples that have been amplified, sequenced, and run on the ABI PRISM 3700/3730xl DNA Analyzer.

Principle:
  The DNA sequencing reactions are electrophoresed, creating a ladder of fluorescently labeled DNA products, each differing in molecular weight by one nucleotide base. The four dyes incorporated into the sequenced sample each represent a different nucleotide. The order of the nucleotides is observed from the chromatogram and the analysis of the chromatogram determines the DNA sequence of the allele(s).

Specimen:
  An electronic file of sample information, including run conditions, and the order of the four DNA bases.

Equipment and Software:
  PC computer
  Applied Biosystems DNA Sequencing Analysis software
  Assign™_SBT software Procedure:
A. Sequencing Analysis and Transferring Data from 3730XL DNA Analyzer
  1. After the 3730xl DNA Analyzer has completed its run, remove the plate base with sample plate from the stacker tower and store at 4° C. Samples can be re-run on the 3730xl instrument when needed within 2 days.
  2. Open the Sequencing Analysis 5.1.1 icon on the computer workstation desktop.
  3. Transfer sample run folder to Sequencing Analysis 5.1.1. Under the File menu in the Sequencing Analysis 5.1.1 software, ClickFile→AddSample→MyComputer→LocalDisk(E:)→AppliedBiosystems→UDC→DataCollection→Data→select folder or files for which you wish to do analysis→AddSelectedSample→OK.
  4. Under the Analysis menu in the Sequencing Analysis 5.1.1 software, click Analysis→AnalysisProtocolManager→LRSAnalysis (default setting for HLA class I and II)→Apply to all samples→Done.
  5. Click on the green arrow located on the upper menu bar and all sample files in that run will be analyzed by Sequencing Analysis 5.1.1. Save all samples before closing the sequencing analysis window.
  6. After sequence analysis, transferring data to the network. Drag and drop the sample run folder from:
  My Computer/LocalDisk(E:)/Appliedbiosystems/UDC/Datacollection/Data/sample run folder to→Bigisland/001FILESVR/seqdata/Temp/techs folder B. HLA Allele Analysis with Assign™_SBT
  1. After the 3730xl has completed its run, analyze and transfer the sequence folders from 3730xl to the folder on the network Bigisland/001FILESVR/Temp/techs folder.
  2. Delete all the bad data in sequence folder in Temp. Highlight the sequence folder or files to be analyzed, then drag and drop them to the final folder where the files should go.
  3. Open the Assign software by typing user name and password. Change the Default settings to SBT and Encoding to UTF-8. Then click the Submit button.
  4. After the Analysis window is open, go to File Import, and choose the Selected Files or Directory.
  By Selected Files: Import individual sequencing files
  By Directory: Import Folder
  NOTE: Before importing sample folder or files, make sure the entire sequence file name is in standard format, sample ID_Locus_Primer.
  5. When import is completed, select Sample Name in the Test Sample Pane by using the arrow keys or click the mouse. Then the test sample consensus sequence, the electropherograms (EPG), and the allele assignments of the selected sample appear on the screen. Using the right mouse click enables samples to be added or deleted.
  6. Move the Editor bar to the very beginning of the sample consensus sequence in the Sequence Pane.
  7. The Assignment Pane displays information about the best matched pair of alleles from the current library. Make sure the sequence is complete by checking the Full Number, which indicates the appropriate sequence length.
  8. Click N from the tool bar to open the Navigator window.
  9. Make sure the BCS and Mismatch box are selected. Click the >> or the <<, which allows you to move the Editor to the positions that have low BCS (score <30) or are mismatched with the allele pairs in the Assignment Pane. If it is necessary, click the button > or <, which allows you to move the Editor to a single base in either direction.

10. Correct the sample consensus sequence by deselecting the wrong base buttons first. Then select the correct base buttons in Navigator.
11. After all the sequence files are checked and edited, select File Save to save as the same name as your current sequence Folder name. Then select Reports/Report Generator from the menu bar.
    NOTE: In order to re-open a saved file, the original electropherograms must be kept in the same location. Do not change the folder ID name after a file is saved.
12. Click Allele Report, make a check on Match Summary: NMDP codes and Edit List sort by locus. Select Excel as output format, then click the Generate Report button.
    NOTE: An allele assignment cannot always be considered correct when its number of mismatches indicated is 0, unless the whole sequence is checked from beginning to the end as correct.
13. Make Assign XML report by selecting XML as output format, then click the "Generate Report" button. Save as (seqdata) R:\ data_2013 report/.
14. Import the Assign xml report into Allelos.

Example 9

Operation and Maintenance of the Biomek NX Multichannel Automation Workstation

This example, which has been reduced to practice, describes how to prepare for a run on the Beckman Coulter Biomek NX multichannel automation workstation in order to purify PCR products or clean up sequencing products in a 96- or 384-well format.

Principle:
  The Biomek NX multichannel automation workstation can accurately aliquot in the microliter range (2-200 µL) to a 96- or 384-well format. The robot was selected to provide hands-free automation to rapidly handle specific multi-step protocols; thus, the automated processes of PCR and sequencing product purification (i.e., clean-up) can increase testing capacity and improve the lab operation providing more efficiency and lower cost.

Specimen:
  Unpurified PCR or sequencing products in 96- or 384-well tray format Equipment and Reagents:
  Biomek NX multichannel automation workstation, PC work station with software
  Milli-Q water
  200 Proof ethanol (cat #6505001050000, Warner-Graham Company)
  300 mL 70% ethanol
  200 mL 73% ethanol
  Ampure (#000132, Agencourt)
  CleanSEQ (#000136, Agencourt)
  Semi-skirted 96-well plate (#AB-1400L, Thermo Scientific)
  Thermo-Fast 384 Diamond PCR Plates (#AB-1111, Thermo Scientific)
  AP96 P250 Tips (#717252, Beckman Coulter)
  AP96 P20 Tips (#717255, Beckman Coulter)
  Compressed air, zero grade (R106B3, Roberts Oxygen Company, Inc.)

Procedure:
A. Prepare for PCR amplicon purification:
  1. Turn on the computer and the robot; launch Biomek software, open the protocol file and Ampure 96 methods.
  2. Select AMPure 96 2.45-3.1 Elution Mix protocol.
  3. Click Run button (green arrow); the window of AMPure for Biomex FX Ver2.74 will pop up.
  4. Select 25 µL in PCR Reaction Volume box.
  5. Select Number of PCR plates needing purification.
  6. Click OK, the Biomek software deck map will show up.
  7. Prepare and place the reagents Milli-Q water, Ampure, and 70% ethanol onto their defined position on the instrument deck according to the map of the deck layout.
  8. Properly place the AP96 P250 tips onto the defined position according to the map, set up the 96-well magnet plate onto the defined position according to the map.
  9. Place the clean semi-skirted 96-well plates onto the defined position in the instrument according to the map.
  10. Spin down the PCR product plates (2500 rpm×30 second) and place them onto the defined position in the instrument and double check that the names of PCR plates match the location of their labeled clean plates in the map.
  11. Double-check that all the labware, reagents and their location match the above layout.
  12. If yes, choose OK to continue the method.
  13. If no, choose Abort to stop the method. After correction the problem, re-run the program by clicking the Green Arrow.
B. Prepare for purification of sequencing reactions:
  1. Turn on the computer and robot; launch Biomek software, open the protocol file and open CleanSEQ method.
  2. Prepare and place the reagents Milli-Q water, CleanSEQ, and 73% ethanol according to the map in CleanSEQ method.
  3. If the sequencing reaction product is in a semi-skirted 96-well plate:
     a. Open the CleanSEQ 96 well method
     b. Select cleanSEQ 2.39-3.1 DOD
     c. Click the Green Arrow, the window of CleanSEQ for Biomek FX ver. 2.74 will pop-up.
     d. Select 6 µL in sequencing reaction box
     e. Select 10 µL in CleanSEQ volume.
     f. Select the Number of plate needing purification.
     g. Properly place the AP96 P250 tips onto the defined position according to the map.
     h. Set up 96-well magnet plate onto the defined position according to the map.
     i. Place unused clean semi-skirted 96-well plates onto the defined position in the instrument according to the map.
     j. Spin down the sequencing product plates (2500 rpm×30 second) and place them onto the defined position on the deck of the instrument according to the map.
     k. Double check that all the labware positions match the above map.
     l. If yes, choose OK to continue the method.
     m. If no, choose Abort to stop the method. After correction the problem, re-run the program by clicking the Green Arrow.
  4. If the sequencing reaction product is in a Thermo-Fast 384 Diamond plate:
     a. Open the CleanSEQ 384 well method
     b. Select SEQ 384Quad 2.37-3.1 DOD.

c. Select 7 µL CleanSEQ in reaction makeup box.
d. Select Number of 384 plate or Quadrants need to clean up.
e. Properly place the AP96 P20 tips onto the defined position according to the map.
f. Setup 384-well magnet plate onto the defined position according to the map.
g. Centrifuge the sequencing product plates (2500 rpm×30 second) and place them onto the defined position on the deck of instrument according to the map.
h. Double-check that all the labware positions match the map.
i. If yes, choose OK to continue the method.
j. If no, choose Abort to stop the method. Correct the problem and re-run the program by clicking the Green Arrow.

Example 10

Operation of the Biomek NX Span 8 Automation Workstation with Paradigm DNA Reader This example, which has been reduced to practice, describes how to prepare for a run on the Beckman Coulter Biomek NX Span 8 automation workstation with Paradigm DNA Reader in order to measure DNA concentration of PCR amplified DNA automatically in a 96-well format and do normalization.
Principle:
  The Biomek NX Span 8 with Paradigm DNA Reader automation workstation can accurately read the optical density is DNA concentration of PCR amplified DNA in 96-well plates following a PCR clean-up reaction. Then Biomek NX Span 8 can do normalization by adjusting the DNA concentration automatically so that all samples have the same concentration before performing the sequencing reaction. The Span 8 can accurately aliquot in the microliter range (2-200 µL) to a 96-well format. This robot was selected to provide hands-free automation to rapidly handle specific multi-step protocols, especially the processes of PCR product normalization can increase testing capacity and reduce error.
Specimen:
  Purified PCR products in half area 96-well UV plate
Equipment and Reagents:
  Biomek NX Span 8 automation workstation, PC work station with Biomek software
  Paradigm Detection Platform (Beckman Coulter)
  Milli-Q water
  AP96 P250 Tips (#717252, Beckman Coulter)
  AP96 P20 Tips (#717255, Beckman Coulter)
  Half area 96-well UV plate (#3679, Corning)
Procedure:
  Prepare normalization for purified PCR product:
  1. Turn on the computer and the robot; launch Biomek software, select the Manual Control under the Manu Instrument.
  2. Click Home All Axes, then press OK until the intake in 8 syringes are clear of bubbles.
  3. Exit the manual control.
  4. Open the protocol file and normalization methods, click Run button (Green Arrow).
  5. Enter the number of PCR plate and name that need to process.
  6. Click OK, the Biomek software deck map will show up.
  7. Place the reagents Milli-Q water, onto its defined position on the instrument deck according to the map of the deck layout.
  8. Properly place the AP96 P250 tips and AP96 20 tips onto the defined position according to the map.
  9. Place half area 96-well UV plate with purified PCR product onto the defined position on the instrument deck according to the map.
  10. Double-check that all the labware, reagents and their location match the above layout.
  11. If yes, choose OK to continue the method.
  12. If no, choose Abort to stop the method. After correction the problem, re-run the program by clicking the Green Arrow.

Example 11

Hybridization, Washing, and Detection of Oligonucleotide Probes (LABType® Protocol)

This example, which has been reduced to practice, describes how to detect the hybridization of Sequence Specific Oligonucleotide Probes (SSOP) to amplified DNA using phycoerythrin (PE)-conjugated Streptavidin (SAPE) and oligonucleotide probes which were coupled to fluorescently coded microspheres (beads).
Principle:
  LABType® SSO is a reverse SSO (rSSO) DNA typing system that binds sequence-specific oligonucleotide (SSO) probes to color-coded microspheres to identify HLA alleles. Oligonucleotide probes complementary to the alleles of interest were coupled to fluorescently coded microspheres (beads). Each unique microsphere is color-coded using a blend of different fluorescent intensities of two dyes. DNA amplified with locus- or group-specific biotin-labeled primers is denatured and incubated with SSOP bound to fluorescently coded microspheres. Probes will bind to complementary DNA sequences during hybridization and non-specifically bound probes (beads) are washed away during stringent washes. The probe-bound DNA is then incubated with PE-conjugated Streptavidin (SAPE). Streptavidin binds non-covalently to biotin. Conjugated to a fluorescent dye, such as phycoerythrin, it can be used to detect biotinylated protein and nucleic acids. A positive reaction will be detected by the Luminex system, in which two lasers are used: (1) Classification laser system which has excitation at 635 nm and emission at 675 nm and >712 nm; and (2) Reporter laser system which has excitation at 532 nm and emission at 575 nm±12 nm.
Specimen:
  96-well tray containing amplified DNA generated in LVTS 12.
Reagents and Equipment:
  Denaturation Buffer (DB)
  Neutralization Buffer (NB)
  Hybridization Buffer (HB)
  Bead Mixture (BM)
  SAPE Buffer (SB)
  Wash Buffer (WB)
  PE-conjugated Streptavidin
  Calibration Microspheres (Classification beads and Reporter beads)
  Sheath fluid
  70% Isopropanol
  20% Bleach
  Milli-Q Water Thermal Cyclers (Applied Biosystems 2700 or 2720)
Centrifuge (Hermle Z400 with 221.08 V01 rotor, or Sorvall RT6000B with H1000B rotor, or Eppendorf 5804 with A-2-DWP rotor)
Luminex Analyzers (version 2.3)
X/Y Platform
Luminex Sheath Dispenser (SD)
15 mL conical tubes
Vortex mixer
96-well Hybridization trays (AB-0700 Fisher Scientific)
Pipettes
Paper towels Procedure:

A. Equipment
 1. Turn on Luminex instrument; it requires 30 minute warm up prior to use.
 2. Turn on thermal cycler and start 60° C. hold program to warm the thermal block.

B. Denaturation and Neutralization
 1. Thaw PCR plate at room temperature and centrifuge the tray at 1000×g for 1 min to spin down the PCR products.
 2. Add 2.5 µL of Denaturation Buffer (DB) into a well of a clean 96-well hybridization tray labeled with panel name, locus, initials and date (note tray orientation).
 3. Transfer and mix up and down 5 µL of each amplified DNA sample into a well of the hybridization tray. Incubate at room temperature for 10 minutes.
 4. Add 5 µL of Neutralization Buffer (NB). Vortex the tray and note color change. Place tray on ice.

C. Hybridization
 1. Combine appropriate volume of Bead Mixture (MB) and Hybridization Buffer (HB) as below and then mix by inverting gently.

| Buffer | 1X | 5X | 10X | 100X | 200X |
|---|---|---|---|---|---|
| | All volumes given in µL | | | | |
| Denaturation | 2.5 | 12.5 | 25.0 | 250.0 | 500.0 |
| Neutralization | 5.0 | 25.0 | 50.0 | 500.0 | 1000.0 |
| Bead Mixture | 0.8 | 4.0 | 8.0 | 80.0 | 160.0 |
| Hybridization | 20.0 | 100.0 | 200.0 | 2000.0 | 4000.0 |
| Wash Buffer | 280.0 | 1400.0 | 2800.0 | 28000.0 | 56000.0 |

2. Add 20 µL of hybridization bead mixture to each well and cover with tray seal. Vortex gently making sure the solution does not touch the tray seal.
 3. Place PCR tray into the pre-warmed thermal cycler (60° C.), place pressure pad on top of tray and incubate for 15 minutes.
 4. Place tray in tray holder, remove tray seal and quickly add 50 µL of Wash Buffer (WB) to each well, and cover with tray seal. Centrifuge tray for 5 minutes between 900-1000×g.
 5. Remove seal and flick hard to remove wash buffer. Keep tray inverted and blot tray on paper towels before turning right-side up to remove extra buffer. Quickly add 50 µL of Wash Buffer and centrifuge as above.
 6. Repeat step 5 (Total of 3 washes).
 7. Remove SAPE from refrigerator. Prepare 1×SAPE Solution (SSB) as below during third wash. Store SSB protected from light. Return to refrigerator immediately after use.

| SAPE Solution | 1X | 5X | 10X | 100X | 200X |
|---|---|---|---|---|---|
| | All volumes given in µL | | | | |
| SAPE Stock | 0.25 | 1.25 | 2.5 | 25.0 | 50.0 |
| SAPE Buffer | 27.0 | 135.0 | 270.0 | 2700.0 | 5400.0 |
| Total | 27.25 | 137.5 | 275.0 | 2725.0 | 5450.0 |

D. Labeling
 1. Add 25 µL of 1×SAPE Solution (SSB) to each well, seal the tray and vortex. Place tray into pre-warmed thermal cycler (60° C.) and incubate for 5 minutes.
 2. Remove tray and place in tray holder, remove seal and quickly add 50 µL of Wash Buffer (WB) to each well and cover with tray seal. Centrifuge as above and remove wash buffer by flicking hard. Keep tray inverted and blot tray on paper towels before turning right-side up.
 3. Add 70 µL of Wash Buffer (WB) to each well.

E. Detection and sample reading using Luminex Analyzer version 2.3
 1. Preparation of Luminex Analyzer
  a) Check Sheath Fluid level, change boxes if necessary. Note: If reservoir has run dry, need to prime 2× to remove air.
  b) Check waste and empty if needed.
  c) Check delta calibration temperature and record. If greater than or equal to 3°, perform calibration.
  d) Turn on the equipment for sample reading in the following order: Luminex Analyzer→X/Y Plate→computer→Luminex SD.
  e) The analyzer will automatically start the Warm-Up operation.
  f) Click Prime to prime the system.
  g) Fill the fluid reservoir in the X/Y Plate with 70% isopropanol and then click Alcohol Flush.
  h) Discard alcohol in the fluid reservoir in the X/Y Plate and change to MilliQ water. Perform two washes.
  i) Discard Water in the fluid reservoir in the X/Y Plate and change to Sheath Fluid. If necessary perform calibration as described below:
   Beads Calibration:
   Vortex the calibration microsphere bottles and then put three drops each of Classification beads (CAL-1), Reporter beads (CAL-2), Classification Control beads (CON-1), and Reporter Control beads (CON-2) into four different wells of a hybridization tray.
   Open X/Y plate and place the hybridization tray inside.
   On the Maintenance Tab select the appropriate wells for the CAL-1, CAL-2, CON-1, and CON-2 calibration beads. Make sure the lot numbers of calibration reagents match the lot numbers selected for use in the software.
   On the Home Tab click CAL-1 and the first calibration will begin.
   Perform one Wash Cycle and then click CAL-2. Continue with CON-1 and CON-2 performing one Wash Cycle in between each calibration.
  j) Discard Sheath Fluid in the fluid reservoir in the X/Y Plate and change to Water. Perform three Washes with Water.
  k) Discard Water in the fluid reservoir in the X/Y Plate and change to Sheath Fluid. Perform one Sheath Fluid Wash. The machine now is ready for reading.

2. Place tray to be read into X/Y plate (samples are mixed by the Luminex analyzer prior to data acquisition).
3. On the Home Tab select the appropriate template from the Favorites list. Edit the batch name as follows: panel name (e.g., 2139-W), locus (lowercase), and tech initials (uppercase) e.g., 2139-Wa-HL).
4. Click Load Patient List and select the appropriate file. Make changes to the sample IDs when appropriate (e.g., BLANK to QC-0001). Click Finish.
   NOTE: The .txt file (patient list) must be generated prior to sample acquisition. Using Allelos, click the 'Tray Maps' tab and select 'Load Tray Map'. Enter the name of the "W" tray map and click 'Search'. Double click to open the tray map. Click the 'Action' tab and select 'Export'. The patient list will be exported to: \\001filesvr\lvts\Export Panel IDs.
5. Click Start Plate and the analyzer will perform two washes and then proceed to sample acquisition for the entire tray. The reading time will vary between 10 seconds to 80 seconds on bead count per sample.
6. Once the reading complete, the data will be exported to: \\001filesvr\lvts\NewData\Analyzer (D, E, F, G, H, I, J, or R2).
7. Before reading another panel, perform three Washes with Water and one Wash with Sheath Fluid.
8. After all readings are completed, shut down the system.

F. Recording

Complete the Hybridization and Detection portion of the Luminex HLA Worksheet.

Example 12

Automation Using LABXpress™

This example, which has been reduced to practice, describes LABXpress™, a system for automating routine laboratory tasks such as pipetting and moving microplates. It automates many of the steps involved in preparing and reading One Lambda's LABType® assays.

Principle:
The principle is the same as in Example 11.

Specimen:
96-well tray containing amplified DNA generated in Example 4.

Reagents and Equipment:
Denaturation Buffer
Neutralization Buffer
Hybridization Buffer
Bead Mixture
SAPE Buffer
Wash Buffer
PE-conjugated Streptavidin
Calibration Microspheres (Classification beads and Reporter beads)
Sheath fluid
70% Isopropanol
20% Bleach
Milli-Q Water
WD-40 lubricant
LABXpress™ (includes computer, thermal cycler, centrifuge, Luminex)
Vortex mixer
96-well Robotic plates (AB-1300 Fisher Scientific)
96-well tray lids (B70651-MidSci)
5 mL polypropylene snap cap tubes with lids and barcodes
LABXpress™ bar-coded reservoirs and loading racks
Pipettes Procedure:
A. Preparing LABXpress™:
   1. Turn on the computer, LABXpress™, thermal cycler, and centrifuge.
   2. Log onto the computer and open the LABXpress Commander. Click "Yes" to Initialize the robot.
   3. Add approximately 5 mL of 70% Isopropanol to the appropriately labeled reservoir, place into a loading rack, and load onto first lane of LABXpress™.
   4. Click File→Open→Maintenance→AlcoholFlush_$1^{st}$.rss. Click the Start Script button (green arrow).
   5. When the alcohol flush is complete, click File→Open→Maintenance→SystemFlush_$2^{nd}$.rss. Click the Start Script button.
   6. When the system flush is complete, click File→Open→Maintenance→WashHead_Maintenance.rss. Click the Start Script button.

B. Preparing the Luminex:
   1. Turn on the Luminex analyzer, X/Y Platform and the Sheath Dispenser. The Luminex analyzer needs 30 minutes to warm up before calibration can be performed.
   2. Open the Luminex software on the computer and run a Prime.
   3. Add 70% Isopropanol to the reservoir and run an Alcohol Flush.
   4. Next replace the 70% Isopropanol with Milli-Q Water and run 3 washes.
   5. Replace the Milli-Q Water with Sheath Fluid and run 1 wash.
   6. After the lasers are warmed up, run the calibration and control beads (CAL-1, CAL-2, CON-1 and CON-2) as described in Example 11.
   7. After calibration, run three water washes and one sheath fluid wash.

C. Preparing the Daily Run:
   1. Remove up to 16 trays of amplified DNA from the freezer and spin briefly to remove condensation.
   2. Transfer 5 ul of amplified DNA to clearly labeled (plate and locus) 96-well robotic plates. Place lids (96-well plates) loosely on robotic trays to prevent evaporation.
   3. Place up to the first 8 trays on the LABXpress™ deck. Additional trays can be aliquotted as needed throughout the day.
   4. Prepare the bead mixtures in 5 mL polypropylene tubes that have been labeled with the locus (3839 µL of hybridization buffer and 82 µL of vortexed locus-specific beads). The LABXpress™ will ensure proper mixing before using the bead mix.
   5. Using Appendix II, prepare the appropriate amount of Denaturation Buffer, Neutralization Buffer and SAPE Mixture (one reservoir of each reagent is sufficient for up to 16 trays). Wash Buffer does not need to be measured as one full reservoir is required for each tray.

D. Starting the Daily Run:
   1. Close the LABXpress Commander software and the Luminex software.
   2. Open the Fusion software and login.
   3. Select LABXpress→Run Monitor. Enter the Assay Type (LABType) and the Run Type (Express-Plate Driven). Click "GO" and enter the number of plates to be run.
   4. Double-click on each plate name and select "Select by Test/Luminex Patient List". Click the " . . . " box and select appropriate path to the desired patient list (e.g., -M\Exported Panel IDs\6541-Y).
5. Edit the tray name to adhere to the standard format (e.g., −6541-Ya-CM).
6. Continue until all patient lists/tray names are entered. Click "Run". Fusion will connect the instruments at this time and open both the LABXpress Commander and the Luminex software.
7. Initialize the robot using the LABXpress Commander software. After the robot has initialized, click "OK" on the Fusion pop-up box.
8. Click "OK" to begin reagent loading. Load the first rack of reagents. Make sure the bar-code reader correctly scans each reagent (indicated by green dots on the screen). When reagent loading is complete, click the "Accept" button. All buffers are loaded in the wide bar-coded reservoirs and should be loaded in the first five rows. It is recommended to load the reservoirs empty to avoid spilling reagents in the loading bay. The bead mix tubes are loaded into the last row of the loading bay. It is recommended that empty bar-coded tubes be loaded and then replaced with the actual bead mixes.
9. When the "Template Selection" box pops up, enter the appropriate Luminex templates and click "Save". Now the LABXpress™ should run independently until all trays have been hybridized and all sessions have been acquired on the Luminex. This should take approximately 23 hours for 16 trays.

Example 13

Interpretation and Reporting of HLA SSOP Hybridization Data Using HLA FUSION™ and ALLELOS Software This example, which has been reduced to practice, describes a method to interpret SSOP data generated by Luminex technology and to report results.

Principle:
In HLA typing by sequence specific oligonucleotide probe (SSOP) hybridization, labeled probes hybridized to target DNA sequences that have been amplified by the polymerase chain reaction (PCR). The end result is a pattern of positive and negative probe "hits" that must be interpreted to assign a HLA phenotype at a given HLA locus.

LABType™ SSO is a DNA typing test used for the detection and identification of specificities of HLA alleles. The test applies Luminex technology to the rSSO DNA typing method. A flow analyzer, the Luminex 100, identifies test reactivity measured in fluorescence intensity. LABType® SSO is a reverse SSO (rSSO) DNA typing system that binds sequence-specific oligonucleotide (SSO) probes to color-coded microspheres to identify HLA alleles.

HLA Fusion™ Software is a companion to One Lambda's LABType™ SSO HLA Typing Tests. This software allows one to import raw data from the Luminex 100 flow analyzer after running a LABType™ SSO typing test; to analyze the raw data and review the results in graphical form; to adjust cut-off values to clarify the results, if necessary; and to make allele assignments.

Each locus is tested with a catalog number (e.g., RSSOH1A_002N_00) that utilizes a specific allele database. The HLA Fusion™ program maintains a table of data that includes allele specificity for each probe in a test panel or catalog. Initially, the program uses data from this table to generate a list of haploid patterns that match the probe reactivity for each allele. These so-called "haploid patterns" represent the positive and negative reactions that every possible amplified allele will have with each probe in a panel. The haploid patterns are essentially the "hit" patterns for each allele. After haploid patterns are generated, the program generates a list of phenotype patterns. The phenotype patterns represent the positive and negative probe "hits" for all possible combinations of the haploid patterns. Once sample results are scored according to the cut-off values of probes in the panel, the program compares the entered probe hit to the list of known phenotype patterns. If the entered probe hits match a phenotype pattern, the program will assign the corresponding type. If the entered probe hits match more than one phenotype pattern, the program displays a list of all possible types. Sometimes the entered probe scoring does not match any of the phenotype patterns. In this case, the program allows you to perform up to four false match analyses. If there is no matched phenotype pattern found, no type is assigned and manual evaluation is necessary.

Specimen:
Raw data generated by Luminex.100 analyzer.

Equipment and Materials:
Computer
HLA Fusion™ Software
PCR amplification/Hybridization and detection worksheet (Example 4)
Allelos Software Procedure:
1. Analysis of Typing Results:
  A. Access the HLA Fusion™ Software.
  B. Input Raw Data: Click on the Analyze Data button and select Typing and then select LABType. Click the 'Include Imported CSVs' box and then click on the yellow folder.
    1. For HD beads: Enter the path to the data that will be analyzed (e.g., LVTS on 001file svr/NewData/AnalyzerD/5050-Zb-YZ_ID161/Output) and click Open. Make sure the correct catalog has been selected and click Import. The name of the file will be automatically changed (e.g., 5050-Zb-YZ_ID161_HD) and the file will be available in the HLA Fusion™ Navigator.
    2. For non-HD beads: Enter the path to the data that will be analyzed (e.g., LVTS on 001filesvr/NewData/AnalyzerD/Output/4970-Zc-JBE_ID 68.csv). Make sure the correct catalog has been selected and click Import. Do not select the 'output' file from the original folder because the name will not be correct (all files will be named 'output'). The file will be available in the HLA Fusion™ Navigator.
  C. Primary Analysis of Test Data: See the Analysis Screen Overview section for additional information.
    1. Select the file to be analyzed using the HLA Fusion™ Navigator (the session will be analyzed automatically).
    2. Click on the 'Bead Analysis' tab and compare the data with the QC data. If necessary, a global cut-off adjustment can be made by checking the 'Adj. Cut-off' box and clicking the position of the new cut-off. Then click 'OK'. The 'False Reaction Summary' graph suggests which probes may need to be adjusted.

3. Return to the 'Summary' tab and click on the first sample. Review all beads and make any necessary adjustments to individual samples by clicking the green bar for the sample in question (this will open the analysis information for the sample in question. Click the 'Adj. Cutoff' box and click the position of the new cut-off; then click 'OK'.
4. Return to the first sample using the '1<' button on the top of the screen. If the results are acceptable, click the 'Assign>>' button: this will assign and save the results for the current sample and move to the next sample. Continue assigning results until all acceptable samples have been assigned.
5. Return to the 'Summary' tab and click the 'Assigned Allele Code' heading on the summary chart to make sure that results have been assigned for all acceptable samples.
6. Analysis is complete for this session. You may now exit the software or analyze another session.

D. Preparing the Paperwork Binder:
Technicians will prepare a binder containing the paperwork for all loci for each standard (W, X, Y, Z) batch.
1. Print Panel Worksheets: Open the Allelos software and click the 'Tray Maps' tab and select click 'Load Tray Maps'. Enter the first panel ID (e.g., 5019-W). The tray map will appear in the 'tray map' field below. Click on the tray name in the 'tray map' field and all four panel worksheets will appear. Click the 'Action' tab and select 'Print', select 'Print All' and then select the printer. Place a tab labeled with the tray name on the panel worksheet.
2. Print Panel Summary Report: Open the HLA Fusion™ software and click the 'Reports' tab on the main menu. Click 'Find' and all sessions processed within the specified date range (by default last two weeks) will appear. Click on the 'Operator' tab to sort the sessions by technician. Click the box next to the session name and click the 'Reporter' button. Select 'LABType' and then select 'Panel Summary'. Click the 'View Report' button and your report will appear. Print the report using the printer icon (hidden by the down arrow on the task bar). Initial and date the last page. Repeat this process for each session.
3. Print Probe Cut-off Log (QC Overview): Open the HLA Fusion™ software and click the 'Reports' tab on the main menu. Click 'Find' and all sessions processed within the specified date range (by default last two weeks) will appear. Click on the 'Operator' tab to sort the sessions by technician. Click the box next to all four session names for a single locus (e.g., 5019-Wa, 5020-Xa, 5021-Ya, and 5022-Za) and click the 'Reporter' button. Select 'LABType' and then select 'QC Overview'. Click 'View Report' and print the report using the printer icon (hidden by the down arrow on the task bar). Initial and date the top of each page. Repeat this process for each locus Assembling the Binder in the following order:
    Probe Cut-off Logs (A, B, C, DRB1)
    W Panel Worksheet
        A locus PCR worksheet
        A locus panel summary report
        B locus PCR worksheet
        B locus panel summary report
        C locus PCR worksheet
        C locus panel summary report
        DRB1 PCR worksheet
        DRB1 panel summary report
    Complete the binder in the same manner with the paperwork from the X, Y, and Z panels. Give the binder to the supervisor.

2. Reviewing and Reporting Typing Results:
A. Secondary Analysis of Test Data:
The supervisor or designee will review and confirm the assigned results for each sample.
1. Using the HLA Fusion™ Navigator, open the session to be reviewed. Make sure that no samples have been excluded (technicians may 'exclude' samples that have failed in order to facilitate bead review—all samples must be 'confirmed' in order to be imported into Allelos software) and click the 'Replace XX Code' button (samples with 'XX' codes will be rejected by NMDP).
2. Click on the first sample to open the analysis screen. Scroll through the beads and check the probe cut-off adjustments made by the technician. Note any additional changes on the QC Summary print-out. Click 'Assign>>', 'Save>>', or 'Confirm>>' before navigating to another sample whenever a cut-off adjustment is made or else the cut-off changes will not be saved.
3. Return to the first sample using the '1<' button on the top of the screen. If the results are acceptable, click the 'Confirm>>' button: this will confirm the assigned results for the current sample and move to the next sample. Continue confirming results until all acceptable samples have been confirmed.
4. Review comments made by previous reviewer.

B. Reporting Results (to NMDP):
Confirmed typing results are imported from HLA Fusion™ into Allelos software and are reported to NMDP. All samples within the session must be 'confirmed' in HLA Fusion before the session can be imported into Allelos.
1. Open the Allelos software and click 'SSO' then select 'Import Results'.
2. The status of each sample is automatically set to Unapproved or REDO-SSO. Highlight all unapproved samples that are ready to report and right click to set the status to 'Approved'. If necessary, change the status of REDO samples to reflect any additional testing (e.g., REDO-Bw4). Repeat this process for all sessions that have been imported and then click 'Done'.
3. Click 'Reporting' and select 'Generate SSO NMDP Report'. Click the 'Search' button, select the session to be reported, and then click 'Next'. All samples that are available for reporting are checked by default. If necessary, de-select any samples that do not need to be reported then click 'Next'.
4. The XML report is automatically generated and is visible in the Report window. Assign a report name in the following format: mmddyylocus_trays (e.g., 010709C_5019-22). Make sure all report options and email recipients are correct and click 'Generate and Send'. A box will appear indicating that 'Your report was successfully sent to the NMDP'.

C. Reporting Results (Non-NMDP):
1. Open Allelos software and click 'SSO' then select 'Import Results'.
2. The status of each sample is automatically set to Unapproved or REDO-SSO. Highlight all unapproved samples that are ready to report and right click to set the status to 'Approved'. If necessary, change the status of REDO samples to reflect any additional testing (e.g., REDO-Bw4). Repeat this process for all sessions that have been imported and then click 'Done'.

3. Click 'Reporting' and select 'Generate External Report'. Click the 'Search' button, select the session to be reported, and then click 'Next'. All samples that are available for reporting are checked by default. If necessary, de-select any samples that do not need to be reported then click 'Next'.
4. The Excel report is automatically generated D. Analysis Screen Overview:

Summary Chart Tab: When a session is opened, the summary chart appears. The summary chart lists all samples within the session and data such as assignments, status, analysis date, minimum bead count, and exon control values. The data that is listed can be changed by the 'Field Chooser' button on the left side of the chart header. Above the summary chart is a graph that lists samples as a multiple match (ambiguity), single match, false (one false reaction) or a miss (multiple false reactions or a failed sample). The analysis screen for any sample can be opened by clicking on the sample in the graph or the chart. Click '<<Summary' in the header of the analysis screen to return to the Summary Chart Tab. The 'Auto Accept All' button at the bottom of the screen will assign the NMDP results for all samples with possible assignments. The 'Replace XX Code' button will re-analyze any samples with an invalid (e.g., 15XX) code and replace it with a valid NMDP code. If a valid NMDP code does not exist for a sample, a new code can be requested from NMDP.

Example 14

PCR Primers

Representative PCR primers are presented in Table 1.

TABLE 1

PCR Primers

| Primer Name | Alt. Name | Sequence 5'-3' | SEQ ID NO: |
|---|---|---|---|
| 3A2 | | GCAGGGCGGAACCTCAGAGTCACTCTCT | 1 |
| 3B1 | | CCATCCCCGGCGACCTATAGGAGATG | 2 |
| 3B1-AC | | AGGCCATCCCGGGCGATCTAT | 3 |
| 3BCln3-12 | CP4 | GGAGATGGGGAAGGCTCCCCACT | 4 |
| 5A2 | | CCCAGACGCCGAGGATGGCCG | 5 |
| 5B1 | | GCACCCACCCGGACTCAGAATCTCCT | 6 |
| 5B3 | | GGGTCCCAGTTCTAAAGTCCCCACG | 7 |
| 5Cln1-61 | | AGCGAGGKGCCCGCCCGGCGA | 8 |
| Bex1-BT | BEX1-BT1 | CCGAACCSTCCTCCTGCTGCTCT | 9 |
| DPB1-Int2-RM | | CAGGAAACAGCTATGACCCCAACCCAAAGTCCCC | 10 |
| DPB-F | | TGTAAAACGACGGCCAGCCCGCAGAGAATTAC | 11 |
| DPB-R_A | | CAGGAAACAGCTATGACGCAGGGTCATGGGCC | 12 |
| DPB-R_B | | CAGGAAACAGCTATGACGCAGGGTCACGGCCT | 13 |
| DQ(2/3/4/5/6)5' | | TGTAAAACGACGGCCAGTTCCTCGCAGAGGATTTCG | 14 |
| DQ2/3/43' | | CAGGAAACAGCTATGACCGTGCGGAGCTCCAACTG | 15 |
| DQ5/63' | | CAGGAAACAGCTATGACCTCTCCTCTGCARGATCCC | 16 |
| DR2 | | GGTGGGTGCTGTTGAAGGT | 17 |
| DR28R | | ACACACACACTCAGATTCCCA | 18 |
| DR3/11/6 | | TGGTGGGCGTTGGGGCG | 19 |
| DRB1-ReverseM | | CAGGAAACAGCTATGACCCACTCACCTCGCCKCTGCAC | 20 |
| DRB1-ReverseM2 | | ACTCACCTCGCCKCTGCAC | 21 |
| G10-PCR-F5' | G10-PCR-F | TGTAATACGACGGCCAGTTTCTTGGAGGAGGTTAAGTT | 22 |
| G1-PCR-F | | TGTAAAACGACGGCCAGTTTCTTGTGGCAGCTTAAGTT | 23 |
| G2-PCR-F2 | | TGTAATACGACGGCCAGTTTCCTGTGGCAGCCTAAGAGG | 24 |
| G3M-PCR-F-5' | | TGTAAAACGACGGCCAGTATCTTGGAGTACTCTACGTC | 25 |
| G4-PCR-F5' | | TGTAATACGACGGCCAGTTTCTTGGAGCAGGTTAAACA | 26 |
| G7-PCR-F2 | | TGTAAAACGACGGCCAGTGGCAGGGTAAGTATA | 27 |

TABLE 1-continued

PCR Primers

| Primer Name | Alt. Name | Sequence 5'-3' | SEQ ID NO: |
|---|---|---|---|
| G8/12-PCR-F2 | | TGTAAAACGACGGCCAGTTCTTGGAGTACTCTACGGG | 28 |
| G9-PCR-F5' | G9-PCR-F | TGTAATACGACGGCCAGTTTCTTGAAGCAGGA | 29 |

Example 15

Sequencing Primers

Representative sequencing primers are presented in Table 2.

TABLE 2

Sequencing Primers

| Primer Name | Alt. Name | Sequence 5'-3' | SEQ ID NO: |
|---|---|---|---|
| 3Aln3-66 | AP4 | TGTTGGTCCCAATTGTCTCCCCTC | 30 |
| 3BCln3-12 | CP4 | GGAGATGGGGAAGGCTCCCCACT | 4 |
| 3Bln3-37 | BP4; Bln3-37 | GGAGGCCATCCCCGGCGACCTAT | 31 |
| 31n2-65 | AP2 | TCGGACCCGGAGACTGTG | 32 |
| 5A1n1-46 | AP1 | GAAACSGCCTCTGYGGGGAGAAGCAA | 33 |
| 5B1n1-57 | BP1 | GGGAGGAGCGAGGGGACCSCAG | 34 |
| 51n2-148 | AP3 | GTTTCATTTTCAGTTTAGGCCA | 35 |
| AP1-M | AP1 | GCCTCTGYGGGGAGAAGCAA | 36 |
| AP3M3 | AP3 | GGTTGGTYGGGGC | 37 |
| BEx3F | BP3 | GGKCCAGGGTCTCACA | 38 |
| BIN3S | NewBP4 | AGGCTCCCCACTG | 39 |
| CEX2F | CP1 | GGGTCGGGCGGGTCTCAGCC | 40 |
| CEX2F-M1 | CP1 | GGAGCCGCGCAGGGA | 41 |
| CEX2R | CP2 | GGAGGGGTCGTGACCTGCGC | 42 |
| Cex3F | CP3 | TGACCRCGGGGCCGGGCC | 43 |
| CP2-M2 | CP2 | GTGGGGGATGRGGAGGGGT | 44 |
| DQB96115B | | CACGTGGCAGGTGTAGACG | 45 |
| DQB96119C | EX3F | GTGACAGATTTCTATCCAG | 46 |
| DRB1FSEQ | F | GTGTCTTCTCAGGAGGC | 47 |
| DRB1RSEQ | R | CGCCCCGCGCCGCGCTCAC | 48 |
| 1n2R | BP2 | GGATCTCGGACCCGGAG | 49 |
| M13F | | TGTAAAACGACGGCCAG | 50 |
| M13R | | CAGGAAACAGCTATGAC | 51 |
| New-CP4 | CP4 | TCCCCACTGCCCYTGGTAC | 52 |
| RBSEQ3 | DR-F | TCAGTGTCTTCTCAGGAGGC | 53 |
| RBSEQ4 | DR-R | CAGCTCACAGGGACTCAG | 54 |

Example 16

PCR Primer Pairs

Representative Class I generic PCR primer pairs are listed in Table 3.

TABLE 3

Class I Generic PCR Primer Pairs

| Locus | Forward Primer | Reverse Primer | Amplify Region | Comment |
|---|---|---|---|---|
| A | 5A2 | 3A2 | Exon2 + Exon 3 | |
| B | BEX1-BT1 | 3B1 & 3B1-AC | Exon2 + Exon 3 | amplify B*73 (3') and B*510102 (5') |
| C | 5Cln1-61 | 3BCln3-12 | Exon2 + Exon 3 | |

Representative DRB1 group-specific PCR primer pairs are presented in Table 4.

TABLE 4

DRB1 Group-Specific PCR Primer Pairs

| PCR Name | Forward Primer | Reverse Primer | Amplify Region | Sequence Primers |
|---|---|---|---|---|
| DRB1*01 | G1-PCR-F | DRB1-ReverseM | Exon 2 | M13F/R |
| DRB1*02 | G2-PCR-F2 | DRB1-ReverseM | Exon 2 | M13F/R |
| DRB1*3/6/11 | G3M-PCR-F-5' | DRB1-ReverseM | Exon 2 | M13F/R |
| DRB1*04 | G4-PCR-F-5' | DRB1-ReverseM | Exon 2 | M13F/R |
| DRB1*07 | G7-PCR-F2 | DRB1-ReverseM | Exon 2 | M13F/R |
| DRB1*08/12 | G8/12-PCR-F2 | DRB1-ReverseM | Exon 2 | M13F/R |
| DRB1*09 | G9-PCR-F | DRB1-ReverseM | Exon 2 | M13F/R |
| DRB1*10 | G10-PCR-F | DRB1-ReverseM | Exon 2 | M13F/R |

Representative DQB1 group-specific PCR primer pairs are presented in Table 5.

TABLE 5

DQB1 Group-Specific PCR Primer Pairs

| Locus | Forward Primer | Reverse Primer | Amplify Region |
|---|---|---|---|
| Q2 | DQ(2/3/4/5/6)5' | DQ2/3/4 3' | Exon 2 |
| Q5 | DQ(2/3/4/5/6)5' | DQ5/6 3' | Exon 2 |

Representative DPB1 group-specific PCR primer pairs are presented in Table 6.

TABLE 6

DPB1 Group-Specific PCR Primer Pairs

| PCR Name | Forward Primer | Reverse Primer | Amplify Region | Sequence Primers | Comment |
|---|---|---|---|---|---|
| DP Intron PCR | DPB-F | DPB1-Int2-RM | part Intron 1 + Exon 2 + Part Intron 2 | M13F + M13R + DP341AR | with M13 tail |
| DP A Group PCR | DPB-F | DPB-R A | Exon 2 | M13F + M13R | Amp. Region from base 109 to 340, with M13 tail |
| DP B Group PCR | DPB-F | DPB-R B | Exon 2 | M13F + M13R | Amp. Region from base 109 to 340, with M13 tail |

Example 17

Sequencing Primer Pairs

Representative regular Class I sequencing primer pairs are presented in Table 7.

TABLE 7

Regular Class I Sequencing Primer Pairs

| Locus | Forward Primer | Reverse Primer | Sequencing Region |
|---|---|---|---|
| A | AP1-M | 3ln2-65 | Exon 2 |
| A | 5ln2-148 | 3Aln3-66 | Exon 3 |
| B | 5Bln1-57 | ln2R | Exon 2 |
| B | Bex3F | BIN3S | Exon 3 |
| C | CEX2F-M1 | CP2-M2 | Exon 2 |
| C | Cex3F | New-CP4 | Exon 3 |

Representative Class II sequencing primer pairs are presented in Table 8.

TABLE 8

Class II Sequencing Primer Pairs

| Locus | Sequencing Name | Forward Primer | Reverse Primer | Sequencing Region |
|---|---|---|---|---|
| DQB1 | Q2 | M13F | M13R | Exon 2 |
| DQB1 | Q5 | M13F | M13R | Exon 2 |
| DPB1 | DPB1 | M13F | M13R | Exon 2 |
| DRB1 | DRB1 | M13F | M13R | Exon 2 |
| DRB1 | DRB1-intron | RBSEQ3 | RBSEQ4 | Exon 2 |

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A kit, comprising
a first set of oligonucleotide primers for polymerase chain reaction (PCR) amplification of at least one human leukocyte antigen (HLA) class I locus, at least one HLA class II locus, or both at least one HLA class I locus and at least one HLA class II locus of a subject; and
a second set of oligonucleotide primers for performing one-step DNA sequencing of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject,
wherein: each oligonucleotide primer of the first set of oligonucleotide primers comprises a non-nucleotide detectable tag or marker;
the first set of oligonucleotide primers comprises at least two primers comprising a nucleotide sequence selected from the group consisting of SEQ ID NOs: 1, 5, 6, 9-15, and 19-29; and
the second set of oligonucleotide primers comprises at least two primers comprising a nucleotide sequence selected from the group consisting of SEQ ID NOs: 32, 33, 37, 39, 40, 42-48, and 50-54.

2. The kit of claim 1, wherein the at least one HLA class I locus is selected from the group consisting of HLA-A, HLA-B, and HLA-C.

3. The kit of claim 1, wherein the at least one HLA class II locus is selected from the group consisting of HLA-DRA, HLA-DRB1, HLA-DRB3, HLA-DRB4, HLA-DRB 5, HLA-DQA1, HLA-DQB1, HLA-DPA1, and HLA-DPB1.

4. The kit of claim 1, wherein the at least one HLA class II locus comprises HLA-DRB1.

5. The kit of claim 1, wherein the at least one HLA class I locus comprises HLA-A and HLA-B, and the at least one HLA class II locus comprises HLA-DRB1.

6. A system, comprising
a first set of oligonucleotide primers for polymerase chain reaction (PCR) amplification of at least one human leukocyte antigen (HLA) class I locus, at least one HLA class II locus, or both at least one HLA class I locus and at least one HLA class II locus of a subject;
a second set of oligonucleotide primers for performing one-step DNA sequencing of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject; and
a set of oligonucleotide probes for performing sequence-specific probe hybridization of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject,
wherein:
each oligonucleotide primer of the first set of oligonucleotide primers comprises a non-nucleotide detectable tag or marker;
the first set of oligonucleotide primers comprises at least two primers comprising a nucleotide sequence selected from the group consisting of SEQ ID NOs: 1, 5, 6, 9-15, and 19-29; and
the second set of oligonucleotide primers comprises at least two primers comprising a nucleotide sequence selected from the group consisting of SEQ ID NOs: 32, 33, 37, 39, 40, 42-48, and 50-54.

7. A method for human leukocyte antigen (HLA) typing, comprising
performing one-step DNA sequencing of at least one HLA class I locus or at least one HLA class II locus of a subject, thereby providing at least intermediate resolution typing for the at least one HLA class I locus or the at least one HLA class II locus;
performing sequence-specific probe hybridization for the at least one HLA class I locus or the at least one HLA class II locus, thereby providing a second at least intermediate resolution typing for the at least one HLA class I locus or the at least one HLA class II locus; and
assigning, based on results of the one-step DNA sequencing and the sequence-specific probe hybridization, a single G-level genotype for the at least one HLA class I locus or the at least one HLA class II locus of the subject,
wherein the performing one-step DNA sequencing of at least one HLA class I locus or at least one HLA class II locus of the subject comprises using a set of oligonucleotide primers comprising at least two primers comprising a nucleotide sequence selected from the group consisting of SEQ ID NOs: 32, 33, 37, 39, 40, 42-48, and 50-54.

8. The method of claim 7, wherein the at least one HLA class I locus is selected from the group consisting of HLA-A, HLA-B, and HLA-C.

9. The method of claim 7, wherein the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

10. The method of claim 7, wherein the at least one HLA class II locus comprises HLA-DRB1.

11. The method of claim 7, wherein the at least one HLA class I locus comprises HLA-A and HLA-B, and the at least one HLA class II locus comprises HLA-DRB 1.

12. A method for human leukocyte antigen (HLA) typing, comprising
amplifying DNA encoding at least one HLA class I locus or at least one HLA class II locus of a subject, thereby providing an amplicon of the at least one HLA class I locus or the at least one HLA class II locus of the subject;
performing one-step DNA sequencing of the amplicon of the at least one HLA class I locus or the at least one HLA class II locus of the subject, thereby providing a first at least intermediate resolution typing for the at least one HLA class I locus or the at least one HLA class II locus;

performing sequence-specific probe hybridization of the amplicon of the at least one HLA class I locus or the at least one HLA class II locus of the subject, thereby providing a second at least intermediate resolution typing for the at least one HLA class I locus or the at least one HLA class II locus; and assigning, based on results of the one-step DNA sequencing and the sequence-specific probe hybridization, a single G-level genotype for the at least one HLA class I locus or the at least one HLA class II locus of the subject, wherein:

the amplifying DNA encoding at least one HLA class I locus or at least one HLA class II locus of the subject comprises using a first set of oligonucleotide primers comprising at least two primers comprising a nucleotide sequence selected from the group consisting of SEQ ID NOs: 1, 5, 6, 9-15, and 19-29; and the performing one-step DNA sequencing of at least one HLA class I locus or at least one HLA class II locus of the subject comprises using a second set of oligonucleotide primers comprising at least two primers comprising a nucleotide sequence selected from the group consisting of SEQ ID NOs: 32, 33, 37, 39, 40, 42-48, and 50-54.

13. The method of claim 12, wherein the amplifying DNA encoding at least one HLA class I locus comprises amplifying exon 2 and exon 3 of the at least one HLA class I locus.

14. The method of claim 12, wherein the amplifying DNA encoding at least one HLA class I locus comprises using a first oligonucleotide primer for exon 2 and a second oligonucleotide primer for exon 3 of the at least one HLA class I locus, thereby generating a single amplicon comprising exon 2 and exon 3 of the at least one HLA class I locus.

15. The method of claim 12, wherein the amplifying DNA encoding at least one HLA class II locus comprises amplifying exon 2 of the alpha gene of the at least one HLA class II locus.

16. The method of claim 12, wherein the amplifying DNA encoding at least one HLA class II locus comprises amplifying exon 2 of the beta gene of the at least one HLA class II locus.

17. The method of claim 12, wherein the amplifying DNA encoding at least one HLA class II locus comprises a first amplification for use in performing the one-step DNA sequencing and a second amplification for use in performing the sequence-specific probe hybridization.

18. The method of claim 12, wherein the at least one HLA class I locus comprises HLA-A, HLA-B, and HLA-C.

19. The method of claim 12, wherein the at least one HLA class II locus is selected from the group consisting of HLA-DRA, HLA-DRB1, HLA-DRB3, HLA-DRB4, HLA-DRB5, HLA-DQA1, HLA-DQB1, HLA-DPA1, and HLA-DPB1.

20. The method of claim 12, wherein the at least one HLA class II locus comprises HLA-DRB1.

21. The method of claim 12, wherein the at least one HLA class I locus comprises HLA-A and HLA-B, and the at least one HLA class II locus comprises HLA-DRB1.

22. A kit, comprising a first set of oligonucleotide primers for polymerase chain reaction (PCR) amplification of at least one human leukocyte antigen (HLA) class I locus, at least one HLA class II locus, or both at least one HLA class I locus and at least one HLA class II locus of a subject; and a second set of oligonucleotide primers for performing one-step DNA sequencing of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject, wherein:

each oligonucleotide primer of the first set of oligonucleotide primers comprises a non-nucleotide detectable tag or marker;

the first set of oligonucleotide primers comprises at least one primer, the nucleotide sequence of which consists of any one of SEQ ID NOs: 10-15, 20, and 22-29; and the second set of oligonucleotide primers comprises at least one primer, the nucleotide sequence of which consists of any one of SEQ ID NOs: 4 and 30-54.

23. A system, comprising a first set of oligonucleotide primers for polymerase chain reaction (PCR) amplification of at least one human leukocyte antigen (HLA) class I locus, at least one HLA class II locus, or both at least one HLA class I locus and at least one HLA class II locus of a subject;

a second set of oligonucleotide primers for performing one-step DNA sequencing of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject; and a set of oligonucleotide probes for performing sequence-specific probe hybridization of at least one amplicon prepared using the first set of oligonucleotide primers, wherein the at least one amplicon comprises the at least one HLA class I locus, the at least one HLA class II locus, or both the at least one HLA class I locus and the at least one HLA class II locus of the subject, wherein:

each oligonucleotide primer of the first set of oligonucleotide primers comprises a non-nucleotide detectable tag or marker;

the first set of oligonucleotide primers comprises at least one primer, the nucleotide sequence of which consists any one of SEQ ID NOs: 10-15, 20, and 22-29; and the second set of oligonucleotide primers comprises at least one primer, the nucleotide sequence of which consists any one of SEQ ID NOs: 4 and 30-54.

24. A method for human leukocyte antigen (HLA) typing, comprising amplifying DNA encoding at least one HLA class I locus or at least one HLA class II locus of a subject, thereby providing an amplicon of the at least one HLA class I locus or the at least one HLA class II locus of the subject;

performing one-step DNA sequencing of the amplicon of the at least one HLA class I locus or the at least one HLA class II locus of the subject, thereby providing a first at least intermediate resolution typing for the at least one HLA class I locus or the at least one HLA class II locus;

performing sequence-specific probe hybridization of the amplicon of the at least one HLA class I locus or the at least one HLA class II locus of the subject, thereby providing a second at least intermediate resolution typing for the at least one HLA class I locus or the at least one HLA class II locus; and assigning, based on results of the one-step DNA sequencing and the sequence-specific probe hybridization, a single G-level genotype for the at least one HLA class I locus or the at least one HLA class II locus of the subject, wherein:

the amplifying DNA encoding at least one HLA class I locus or at least one HLA class II locus of the subject comprises using a first set of oligonucleotide primers comprising at least two primers comprising a nucleotide sequence selected from the group consisting of SEQ ID NOs: 10-15, 20, and 22-29; and the performing one-step DNA sequencing of at least one HLA class I locus or at least one HLA class II locus of the subject comprises using a second set of oligonucleotide primers comprising at least two primers comprising a nucleotide sequence selected from the group consisting of SEQ ID NOs: 4 and 30-54.

* * * * *